United States Patent
Kolb et al.

(10) Patent No.: US 10,527,589 B2
(45) Date of Patent: Jan. 7, 2020

(54) APPARATUS AND METHOD FOR IN-SITU CALIBRATION OF A PHOTOACOUSTIC SENSOR

(71) Applicant: Infineon Technologies AG, Neubiberg (DE)

(72) Inventors: Stefan Kolb, Unterschleissheim (DE); Alfons Dehe, Reutlingen (DE); Jochen Huber, Wolfach (DE); Franz Jost, Stuttgart (DE); Horst Theuss, Wenzenbach (DE); Juergen Woellenstein, Freiburg (DE)

(73) Assignee: Infineon Technologies AG (DE)

( * ) Notice: Subject to any disclaimer, the term of this patent is extended or adjusted under 35 U.S.C. 154(b) by 475 days.

(21) Appl. No.: 15/258,646

(22) Filed: Sep. 7, 2016

(65) Prior Publication Data

US 2017/0067859 A1    Mar. 9, 2017

(30) Foreign Application Priority Data

Sep. 7, 2015  (DE) .......... 10 2015 217 098

(51) Int. Cl.
*G01N 29/30* (2006.01)
*G01N 29/24* (2006.01)

(52) U.S. Cl.
CPC ......... *G01N 29/30* (2013.01); *G01N 29/2418* (2013.01); *G01N 2291/021* (2013.01)

(58) Field of Classification Search
CPC ............ G01N 29/30; G01N 29/2418; G01N 2291/021; G01N 21/1702; G01J 5/02; G01J 3/42; G06K 9/00624; A61B 8/08
See application file for complete search history.

(56) References Cited

U.S. PATENT DOCUMENTS

| | | | | |
|---|---|---|---|---|
| 3,694,624 A * | 9/1972 | Buchta | ..................... | G01J 3/108 219/505 |
| 5,394,934 A * | 3/1995 | Rein | ........................ | F24F 11/30 165/200 |
| 7,304,732 B1 * | 12/2007 | Polcawich | ......... | G01N 21/1702 250/339.07 |
| 8,930,145 B2 * | 1/2015 | Li | ........................ | A61B 5/0059 600/407 |
| 8,939,006 B2 * | 1/2015 | Rezachek | .......... | G01N 21/1702 356/437 |
| 8,970,842 B2 * | 3/2015 | Sun | ........................... | G01J 3/42 356/432 |

(Continued)

FOREIGN PATENT DOCUMENTS

CN    102596049 A    7/2012

*Primary Examiner* — Harshad R Patel
*Assistant Examiner* — Nigel H Plumb
(74) *Attorney, Agent, or Firm* — Design IP

(57) ABSTRACT

An apparatus for in-situ calibration of a photoacoustic sensor is provided. The apparatus includes a light emitter to emit light along a transmission path to a gas and an acoustic sensor element configured to detect an acoustic signal emitted from the gas based on the received light. Furthermore, the apparatus includes a sensing unit configured to detect the light transmitted along the transmission path and to provide an output signal, and a calibration unit to receive the output signal from the sensing unit and to provide a calibration information based on the output signal received from the sensing unit.

21 Claims, 10 Drawing Sheets

(56) References Cited

U.S. PATENT DOCUMENTS

| | | | |
|---|---|---|---|
| 2011/0106478 A1* | 5/2011 | Someda | A61B 5/0059 |
| | | | 702/104 |
| 2012/0279279 A1 | 11/2012 | Rezachek et al. | |
| 2014/0049777 A1 | 2/2014 | Sun et al. | |
| 2015/0049168 A1* | 2/2015 | Dielacher | G06K 9/00805 |
| | | | 348/46 |
| 2015/0092814 A1* | 4/2015 | Wolfgruber | G01J 5/02 |
| | | | 374/121 |
| 2015/0101395 A1* | 4/2015 | Dehe | G01N 29/2418 |
| | | | 73/24.02 |

* cited by examiner

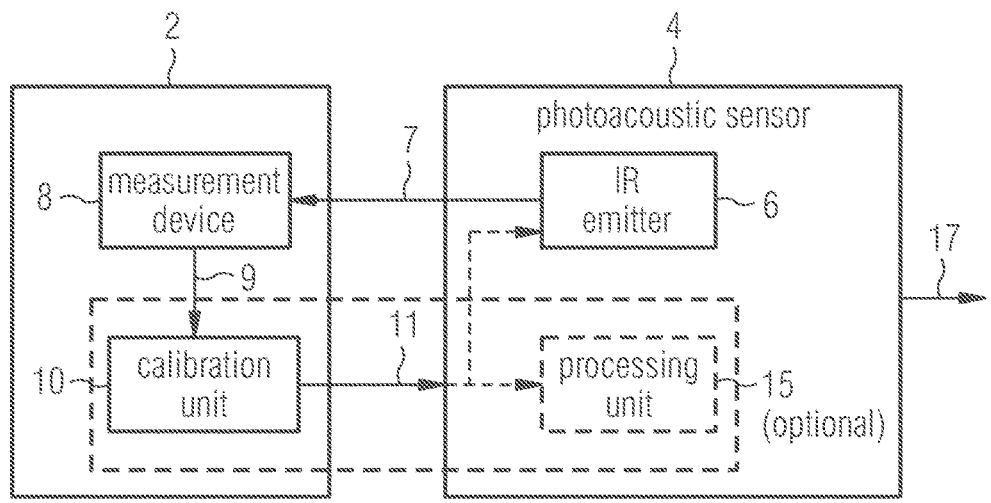
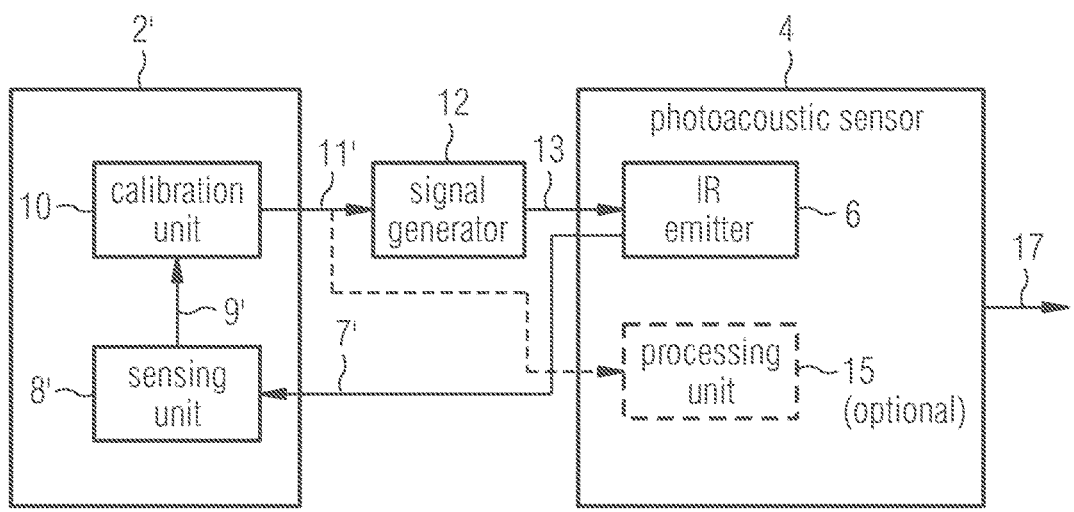

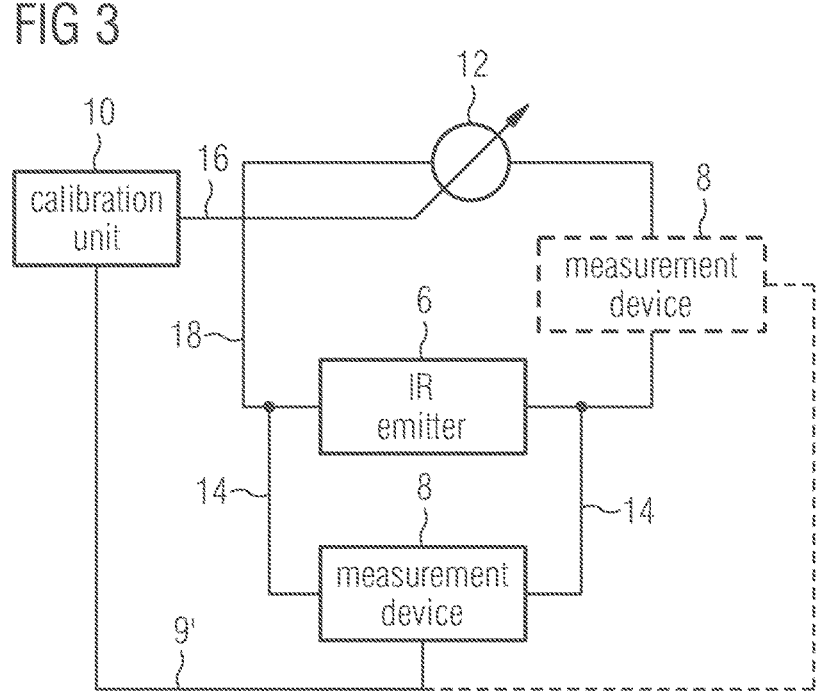
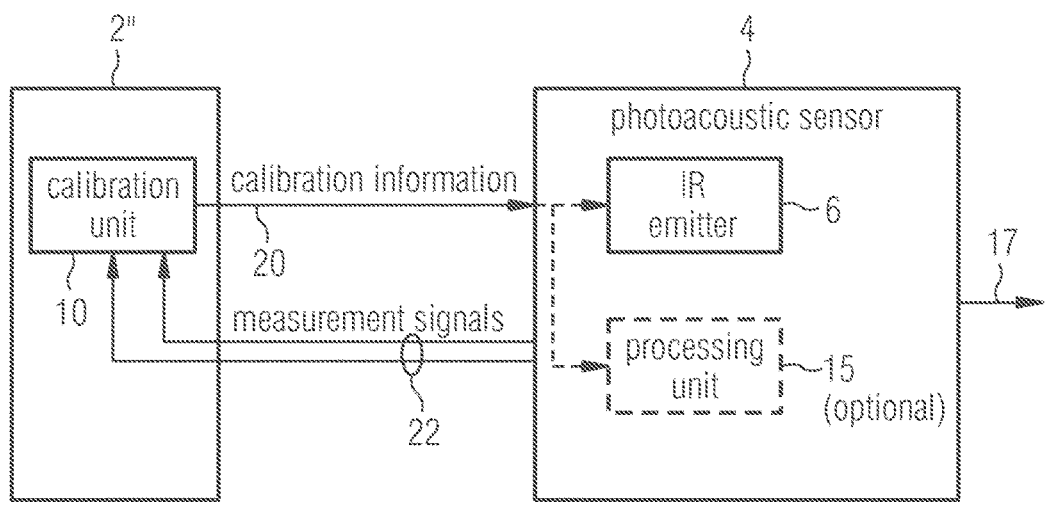

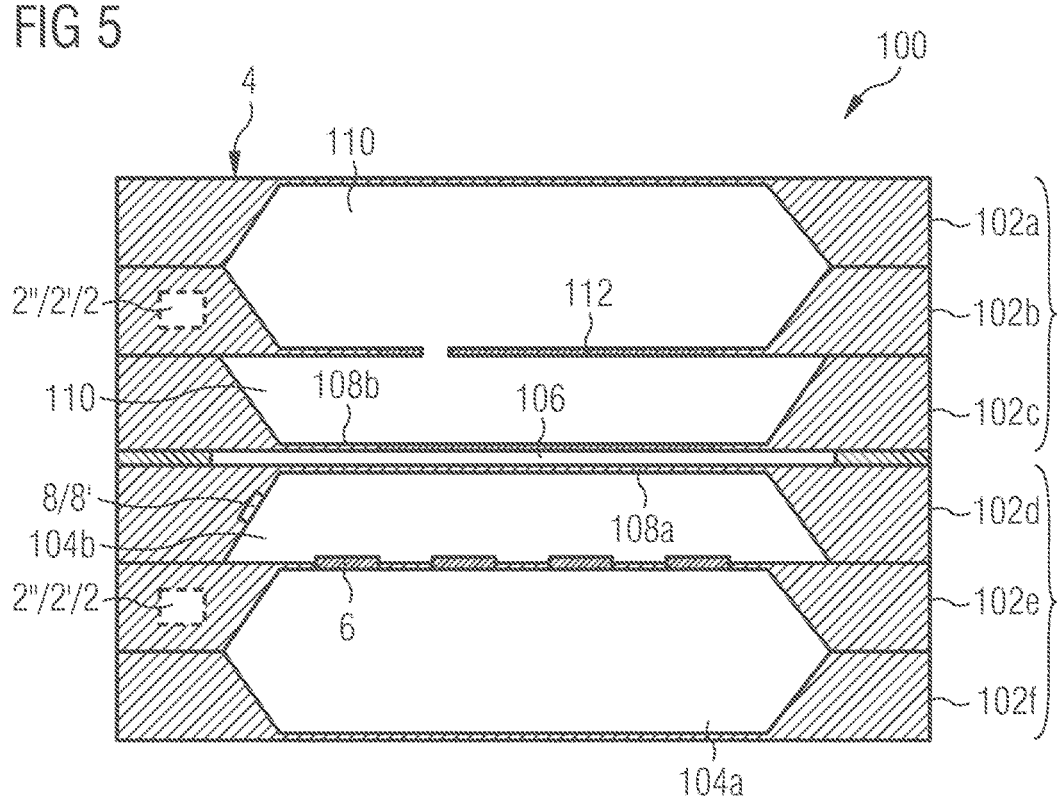

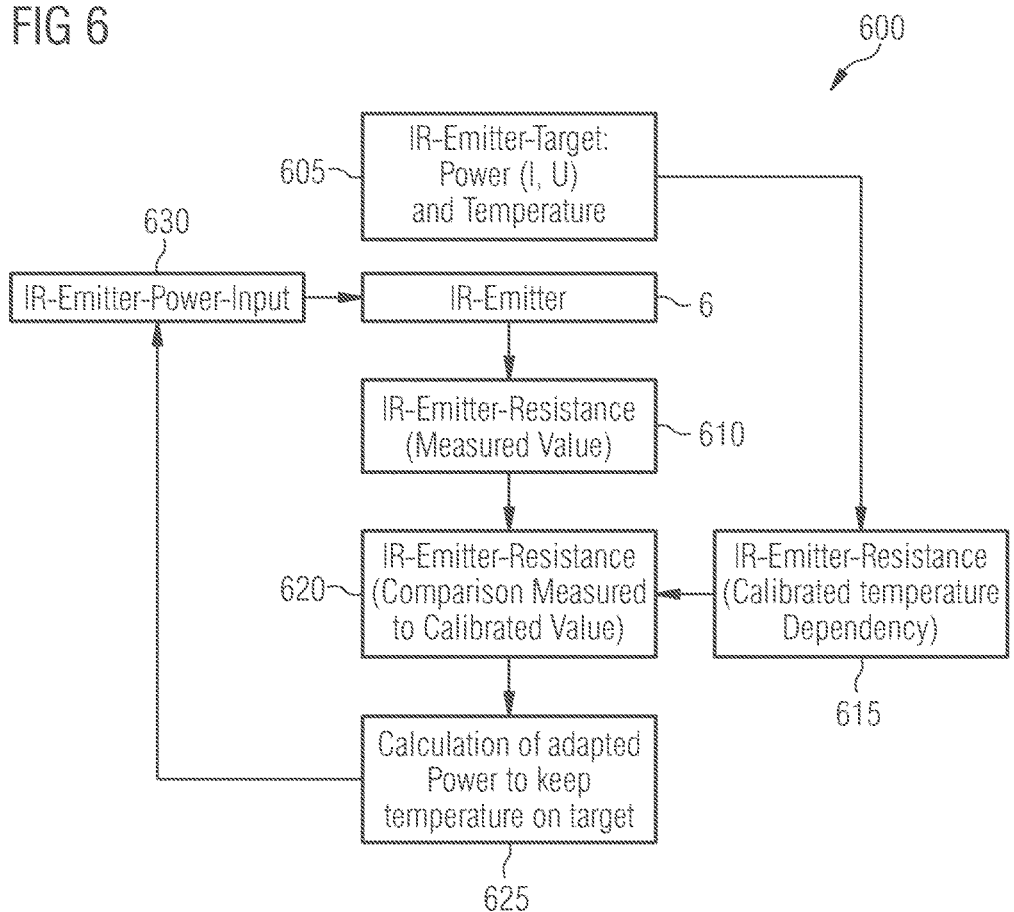

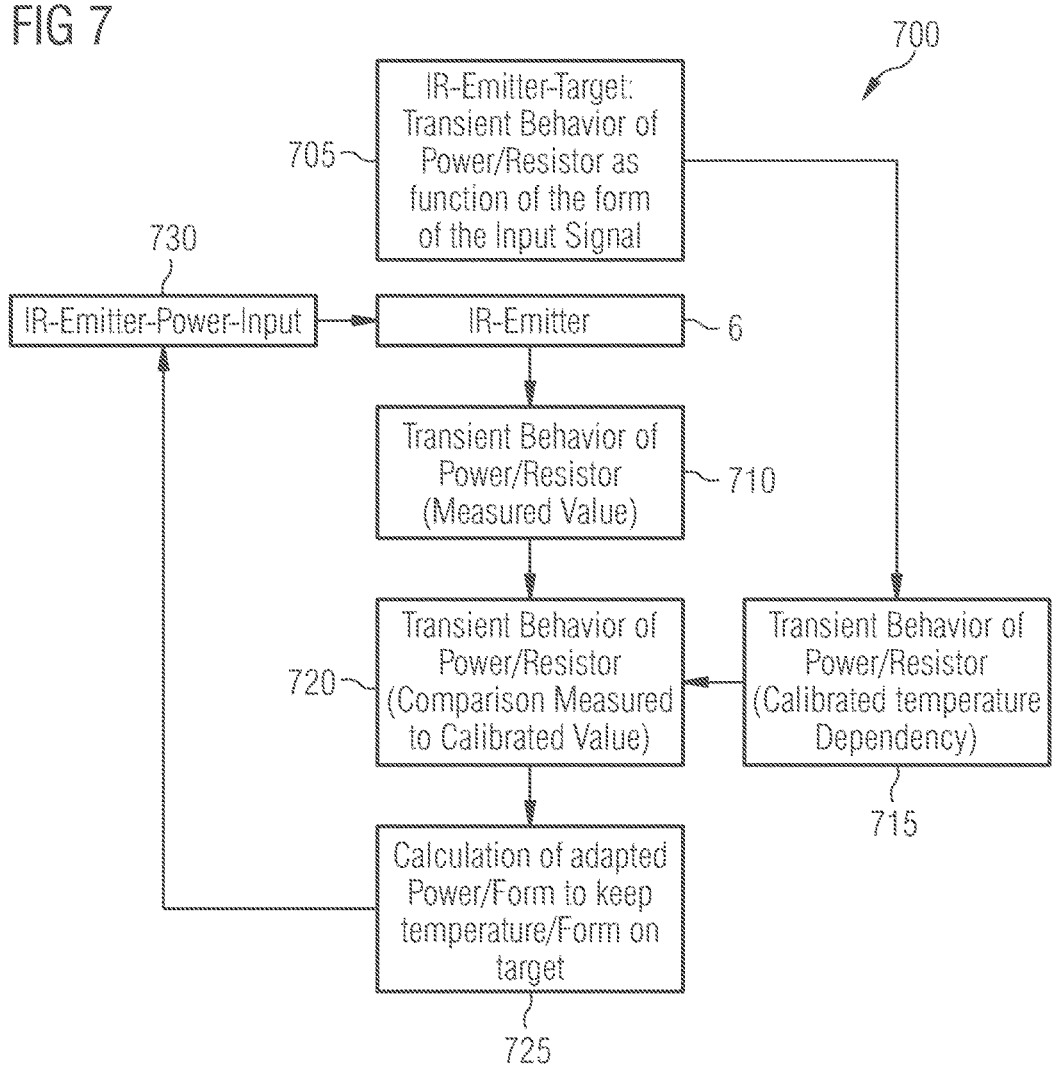

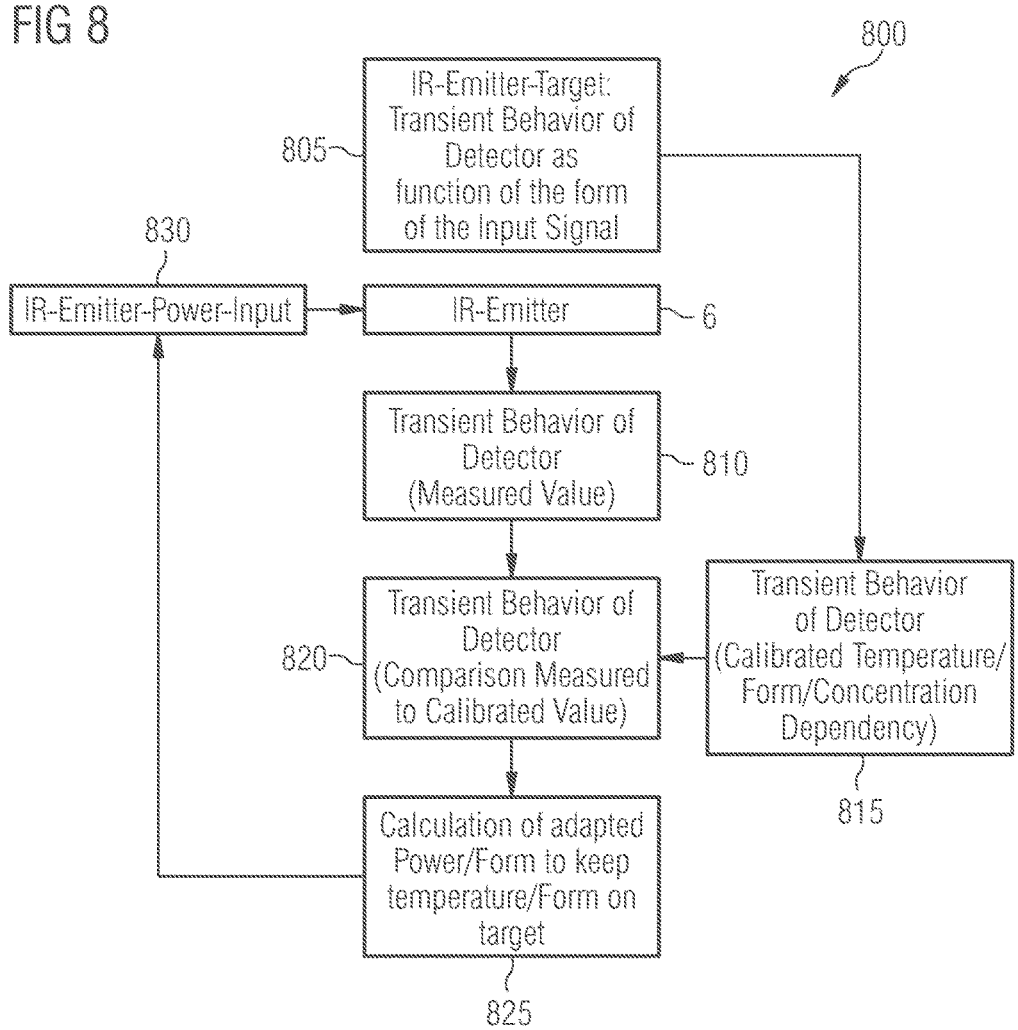

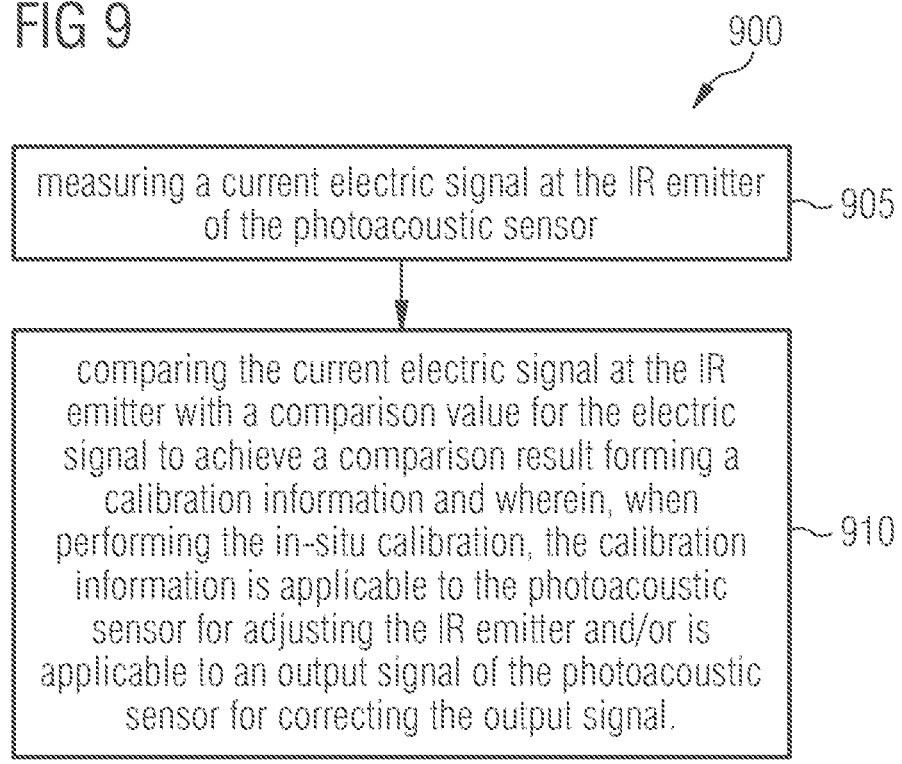

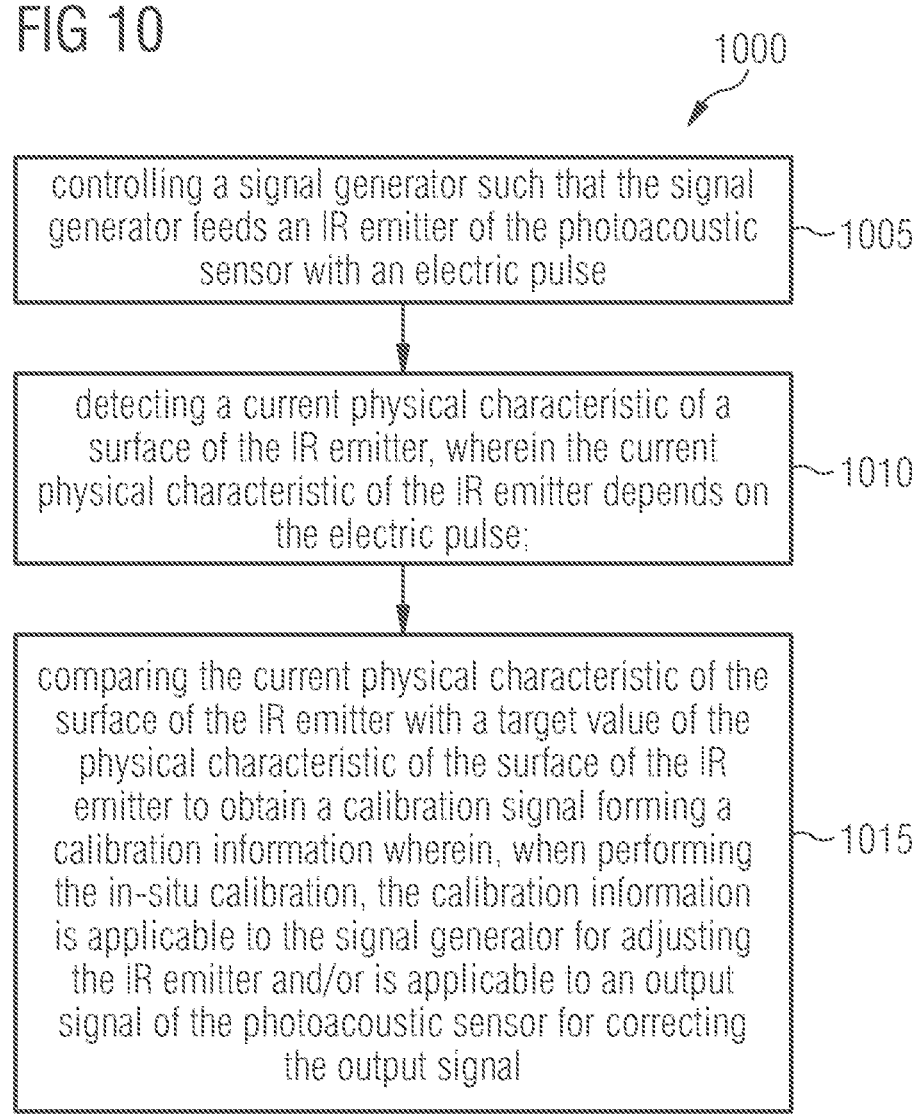

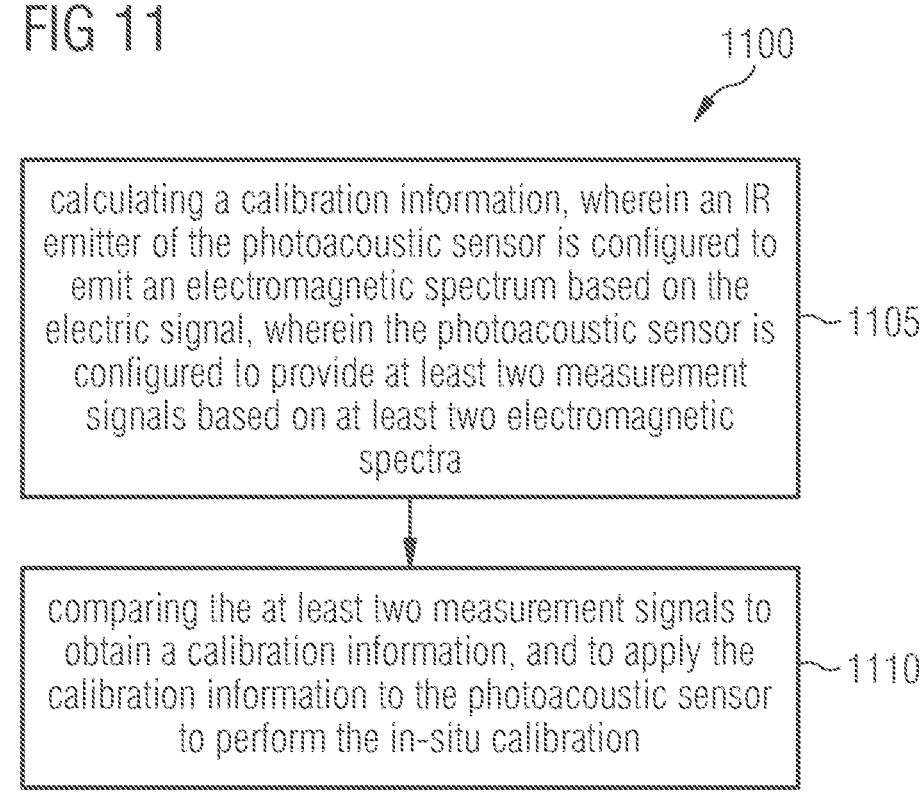

APPARATUS AND METHOD FOR IN-SITU CALIBRATION OF A PHOTOACOUSTIC SENSOR

FIELD

The present disclosure relates to an apparatus and a method for in-situ calibration of a photoacoustic sensor based on calibration information acquired during operation of the photoacoustic sensor.

BACKGROUND

Gas sensors suffer from multiple calibration procedures and a fast replacement of the gas sensors after having a comparably short life cycle. Typical calibration procedures adjust a zero line of the sensor based on a lowest measured value within a predetermined period, such as for example a couple of days. However, it is only applicable for sensors having periods of time, where a gas compound that shall be measured is absent and is therefore limited in its usage. Furthermore, its calibration method is not very precise.

A different calibration procedure may use a reference sensor being in use only for measuring a calibration value and therefore suffering from less degradation than the main sensor which shall be calibrated. However, this is expensive, elaborate, and the whole (photoacoustic) sensor becomes larger since the reference sensor needs to be included.

Therefore, there is a need for an improved approach.

SUMMARY

The in-situ calibration of a photoacoustic sensor may be conducted by adjusting an IR emitter based on the calibration information or by performing a corrected processing of the output signal of the IR emitter (or a signal derived from the output signal). Further embodiments show a microelectromechanical system comprising the apparatus. Further embodiments relate to a (in use) calibration of a photoacoustic sensor (PAS) module.

Embodiments are based on the finding that an in-situ or in use calibration of a photoacoustic sensor may be performed to overcome the aforementioned limitations. Therefore, gas sensors may have a high and steady precision over their whole life cycle. Upcoming, multiple embodiments for in-situ calibration, e.g. related to calibrate the photoacoustic sensor with adjusting an infrared (IR) emitter, are shown.

To be more specific, embodiments are based on the finding that an in-situ or in use calibration of a photoacoustic sensor may be performed based on calibration information which may be derived from a physical parameter or characteristic of the photoacoustic sensor or, for example, of the IR emitter of the photoacoustic sensor, and which are achieved or detected during operation of the photoacoustic sensor. The in-situ calibration of a photoacoustic sensor may be conducted by adjusting an IR emitter based on the calibration information, e.g. by adjusting a control signal fed to the IR emitter and/or by correcting the output signal of the IR emitter (or a signal derived from the output signal).

Moreover, the in-situ calibration of a photoacoustic sensor may be conducted during processing or evaluating the output signal of the IR emitter (or a signal derived from the output signal), wherein the detected calibration information is incorporated into the processing or evaluating of the output signal of the IR emitter (or a signal derived from the output signal). As a result, a corrected (e.g. calibrated) processing or evaluating of the output signal of the IR emitter (or a signal derived from the output signal) can be achieved.

Embodiments relate to an apparatus for in-situ calibration of a photoacoustic sensor e.g. achieved with adjusting an IR emitter. The apparatus comprises a measurement device and a calibration unit. The measurement device is configured to detect or to measure a current electric signal (instantaneous signal) at or through the IR emitter of the photoacoustic sensor, wherein the calibration unit may compare the current electric signal at the IR emitter with a comparison value for the electric signal to achieve a comparison result forming a calibration information. When performing the in-situ calibration, the calibration information is applicable to the photoacoustic sensor for adjusting the IR emitter and/or is applicable to an output signal of the photoacoustic sensor for correcting the output signal. According to embodiments, the calibration unit may adjust the current electric signal based on the comparison result (or the calibration information) to obtain a target electric signal at the IR emitter from the in-situ calibration.

According to further embodiments, the apparatus may comprise an optional processing unit to process the output signal of the photoacoustic sensor based on the calibration information to obtain an adjusted output signal of the photoacoustic sensor. The output signal of the photoacoustic sensor may be a response of an acoustic sensor element such as a microphone of the photoacoustic sensor to the IR radiation of the IR emitter or a gas concentration of a gas component of the measurement gas or a composition of the measurement gas. More specifically, the acoustic sensor element responds to the photoacoustic signal of the measurement gas which is stimulated by the IR radiation or the light emitted by the IR/light emitter. However, the calibration information may be provided to the IR emitter or to the processing unit or to both, the IR emitter and the processing unit. In other words, a direct adjustment of the IR emitter may perform an adjustment of the IR radiation of the IR emitter, wherein an indirect adjustment may calculate a calibration value based on e.g. a deviation of the (current) IR radiation (measure) to a calibrated IR radiation (measure), e.g. using a lookup table, to adjust the output signal of the photoacoustic sensor.

In other words, the apparatus may detect or measure a current voltage (or instantaneous voltage) at the IR emitter or a current electrical current (or instantaneous electrical current) through the IR emitter, for example to calculate a current electric power (or instantaneous electrical power) at the IR emitter, and to adjust the current electric power to a predetermined value or desired value of the electric power. The predetermined or desired value may be obtained from a lookup table or further matching means, mapping the (current) electric power to a temperature or an emissivity of the IR emitter, wherein the emissivity of the IR emitter may refer to an electromagnetic radiation, such as for example an IR or temperature radiation. In other words, the calibration unit may adjust the current electric power such that a target value of a physical characteristic or physical characteristic of the IR emitter is obtained.

Moreover, embodiments show that the calibration unit is configured to adjust the current electric signal such that a change of resistance of the IR emitter is compensated. A change of resistance of the IR emitter may effect a current voltage at the IR emitter or a current electrical current through the IR emitter and therefore effects a power input to the IR emitter. However, the power input of the IR emitter is directly related to a temperature or an emissivity of the IR emitter, resulting in a shifted wavelength of an electromagnetic radiation of the IR emitter. The resistance of the IR emitter may change for example due to a degradation of the IR emitter.

According to further embodiments, the current electric signal comprises an electric pulse, e.g. pulse signal or pulsed signal. Moreover, the calibration unit is configured to calculate a time constant at the further acoustic sensor from the current (or instantaneous) physical characteristic based on the electric pulse, wherein the time constant indicates an ability of the current physical characteristic to follow the electric pulse. In other words, an AC current behavior or, more specifically, a transient behavior of the IR emitter and the current electric signal may be calculated. This behavior may be for example characterized using a time constant, which may be calculated by analyzing an impulse response or a step (function) response of the IR emitter to the electric pulse. Therefore, the electric pulse may be a sine or cosine pulse or signal, a rectangular function or a (proximity of a) Dirac impulse.

Moreover, the calibration unit may be configured to adjust the electric pulse such that at least one of an edge steepness, an amplitude, or a repetition frequency of the electric pulse is changed. The change of the electric pulse (or a sequence of electric pulses or a pulse(d) signal) may also change the physical characteristic of the IR emitters such that the absolute difference between the current physical characteristic and the target value of the physical characteristic is reduced. In other words, the aforementioned sine or cosine wave or pulse, the rectangular signal or the Dirac pulse may be modified such that an electric power at the IR emitter, a temperature of the IR emitter or an emissivity of the IR emitter is adjusted to their target values. Additionally or alternatively, the electric pulse may be only a measurement signal to obtain a calibration value. Therefore, a property characterizing the amount of calibration that has to be performed on the IR emitter, such that for example the time constant, which may be derived from the electric pulse and a measurement signal used for operating the photoacoustic sensor is adjusted based on the property. In general, the current physical characteristic may be different from the target value of the physical characteristic due to a degradation of the IR emitter and wherein the calibration unit may be configured to adjust the electric pulse or in general, the current electric signal, such that a degradation of the IR emitter is compensated.

Further embodiments relate to an apparatus for in-situ calibration of a photoacoustic sensor e.g. achieved with adjusting an IR emitter. The apparatus comprises a calibration unit and a sensing unit. The calibration unit is configured to control a signal generator such that the signal generator feeds an IR emitter of the photoacoustic sensor with an electric pulse or pulse(d) signal. The sensing unit is configured to detect or measure a current physical characteristic of a surface of the IR emitter, wherein the current physical characteristic of the IR emitter depends on the electric pulse. Moreover, the calibration unit may compare the current physical characteristic of the surface of the IR emitter with the target value of the physical characteristic of the surface of the IR emitter to obtain a calibration signal forming a calibration information. When performing the in-situ calibration, the calibration information (or the calibration signal) is applicable to the signal generator for adjusting the IR emitter and/or is applicable to an output signal of the photoacoustic sensor for correcting the output signal.

Therefore, the calibration unit may adjust the electric pulse of the signal generator based on the calibration signal to perform the in-situ calibration. In other words, a temperature or an emissivity, such as for example the ability to emit electromagnetic radiation, may be determined. Therefore, a temperature sensor may measure a temperature of an environment of the IR emitter, which is for example a temperature of a gas surrounding the IR emitter. This may refer to an indirect measurement of the temperature of the IR emitter.

According to further embodiments, the apparatus comprises a processing unit configured to process an output signal of the photoacoustic sensor based on the calibration information (or calibration signal) to obtain an adjusted output signal of the photoacoustic sensor. The output signal of the photoacoustic sensor may be a response of an acoustic sensor element of the photoacoustic sensor to the IR radiation of the IR emitter or a gas concentration of a gas component of the measurement gas or a composition of the measurement gas. However, the calibration information may be provided to the IR emitter or to the processing unit or to both, the IR emitter and the processing unit. In other words, a direct adjustment of the IR emitter may perform an adjustment of the IR radiation of the IR emitter, wherein an indirect adjustment may calculate a calibration value based on e.g. a deviation of the (current) IR radiation (measure) to a calibrated IR radiation (measure), e.g. using a lookup table, to adjust the output signal of the photoacoustic sensor.

Additionally or alternatively, a contactless measurement of temperature radiation, heat radiation, or IR radiation may be performed using for example an infrared detector. More specifically, the sensing unit may be configured to measure a temperature of the surface of the IR emitter using determining a temperature of an environment of the IR emitter or a sensing unit may measure an infrared radiation of the IR emitter at the surface of the IR emitter.

Embodiments further show that the calibration unit may be configured to calculate a time constant of the photoacoustic sensor from the current physical characteristic based on the current electric pulse, wherein the time constant indicates an ability of the current physical characteristic to follow the electric pulse. Furthermore, the calibration unit may adjust the electric pulse such that at least one of an edge steepness, an amplitude, or a repetition frequency of the electric pulse is changed, wherein the change of the electric pulse changes the physical characteristic of the IR emitter such that the absolute difference between the current physical characteristic and the target value of the physical characteristic is reduced. In general, the current physical characteristic may be different from the target value of the physical characteristic due to a degradation of the IR emitter and wherein the calibration unit may be configured to adjust the electric pulse such that the calibration of the IR emitter is compensated. According to further embodiments, the electric pulse may be used for determining only an amount of degradation of the IR emitter, wherein a value indicating the amount of degradation is used to adjust a measurement signal of the IR emitter to operate the photoacoustic sensor during normal operation.

According to further embodiments, the apparatus may comprise the signal generator, wherein the signal generator may be configured to generate the electric pulse and to feed the IR emitter of the photoacoustic sensor with the electric pulse. It is advantageous, since the signal generator may be easily implemented in the apparatus and furthermore, a phase of the combination of the apparatus and the photoacoustic sensor is reduced, since no external signal generator needs to be used. Additionally or alternatively, a signal generator may be further implemented in the photoacoustic sensor.

According to a further embodiment, the apparatus and the IR emitter of the photoacoustic sensor may be formed on a common semiconductor substrate. Furthermore, the sensing unit may comprise a semiconductor temperature sensing unit formed within the semiconductor substrate. One of an easiest way to implement the temperature sensing unit of the semiconductor may be to use a pn junction, or in general, differently doped areas of the semiconductor substrate to form an area within the semiconductor substrate being sensitive to temperature changes. The semiconductor temperature sensing unit may therefore measure a temperature of the environment of the IR emitter, which is approximately a temperature of a surface of the IR emitter and therefore indicates an ability of the IR emitter to heat the environment when compared to an input power of the IR emitter. Additionally or alternatively, a sensing unit may be an infrared sensor being integrated into the semiconductor substrate. This may be, for example, an infrared diode or a bolometer.

Further embodiments relate to an apparatus for in-situ calibration of a photoacoustic sensor. The apparatus comprises a calibration unit configured to calculate a calibration information. An IR emitter of the photoacoustic sensor may emit an electromagnetic spectrum (e.g. an electromagnetic signal or electromagnetic radiation having an electromagnetic spectrum), wherein the photoacoustic sensor is configured to provide at least two measurement signals based on at least two electromagnetic spectra. Moreover, the calibration unit is configured to compare the at least two measurement signals to obtain the calibration information and to apply the calibration information to the photoacoustic sensor to perform the in-situ calibration. In other words, the photoacoustic sensor may perform two different measurements using two different electromagnetic spectra emitted by the IR emitter, advantageously using the same or at least a similar gas for both measurements, and from comparing the resulting measurement signals to derive information about a current performance of the IR emitter when compared to an originally calibrated performance.

Based on the information of how the current performance of the photoacoustic sensor changed with respect to a calibrated performance of the photoacoustic sensor, for example an input power to the IR emitter may be adjusted to recalibrate the photoacoustic sensor or, an analysis of the measurement signals may be adjusted such that for the same gas concentration a current measurement signal and a measurement signal after calibration of the temperature sensor relate to the same result. This may be achieved by, for example, applying an offset to a lookup table, where a current measurement signal and a corresponding gas concentration are stored.

Additionally or alternatively, both approaches may be applied as, for example, the lookup table comprises a comparably rough resolution and the input power to the IR emitter may be slightly adjusted such that a value within the resolution of the lookup table is met. In other words, the major calibration of the photoacoustic sensor may be done using adjusting adapting, modifying, or regulating a relation between the measurement signal and a related temperature or IR emissivity of the photoacoustic sensor. However, the relation between measurement signal and temperature or IR emissivity may be quantized such as e.g. the lookup table. Therefore, the calibration unit may apply an input signal or power on the IR emitter to slightly adjust the temperature or an IR emissivity of the IR emitter such that the quantization steps are met.

In other words, the calibration unit may be configured to control an electric signal at the IR emitter, wherein the IR emitter is configured to emit an electromagnetic spectrum based on the electric signal, and wherein the calibration unit is further configured to adjust the electric signal at the IR emitter based on the calibration information to perform the in-situ calibration. Furthermore, the calibration unit may be configured to calibrate a determination, identification, or specification of a gas concentration in the photoacoustic sensor using the calibration information to perform the in-situ calibration, wherein the determination, identification, or specification of the gas concentration is based on a further measurement signal of the photoacoustic sensor.

BRIEF DESCRIPTION OF THE DRAWINGS

Embodiments of the present invention will be discussed subsequently referring to the enclosed drawings, wherein:

FIG. 1 shows a schematic block diagram of an apparatus for in-situ calibration of a photoacoustic sensor according to a first aspect of one or more embodiments;

FIG. 2 shows a schematic block diagram of an apparatus for in-situ calibration of a photoacoustic sensor according to a second aspect of one or more embodiments;

FIG. 3 shows a schematic functional block diagram of both the first and second aspects according to one or more embodiments;

FIG. 4 shows a schematic block diagram of an apparatus for in-situ calibration of a photoacoustic sensor according to a third aspect of one or more embodiments;

FIG. 5 shows a schematic block diagram of a micromechanical system optionally comprising the apparatus according to one or more embodiments;

FIG. 6 shows a schematic block diagram of a method which may be performed by the first aspect according to one or more embodiments;

FIG. 7 shows a schematic block diagram of a method which may be performed using the second aspect according to one or more embodiments;

FIG. 8 shows a schematic block diagram of a method which may control or calibrate an IR emitter based on a (transient) behavior of the detector signal according to the third aspect according to one or more embodiments;

FIG. 9 shows a schematic block diagram of a method for performing an in-situ calibration of a photoacoustic sensor with adjusting an IR emitter according to one or more embodiments;

FIG. 10 shows a schematic block diagram of a method for in-situ calibration of a photoacoustic sensor according to one or more embodiments;

FIG. 11 shows a method for in-situ calibration of a photoacoustic sensor according to one or more embodiments.

DETAILED DESCRIPTION

Figure 12:
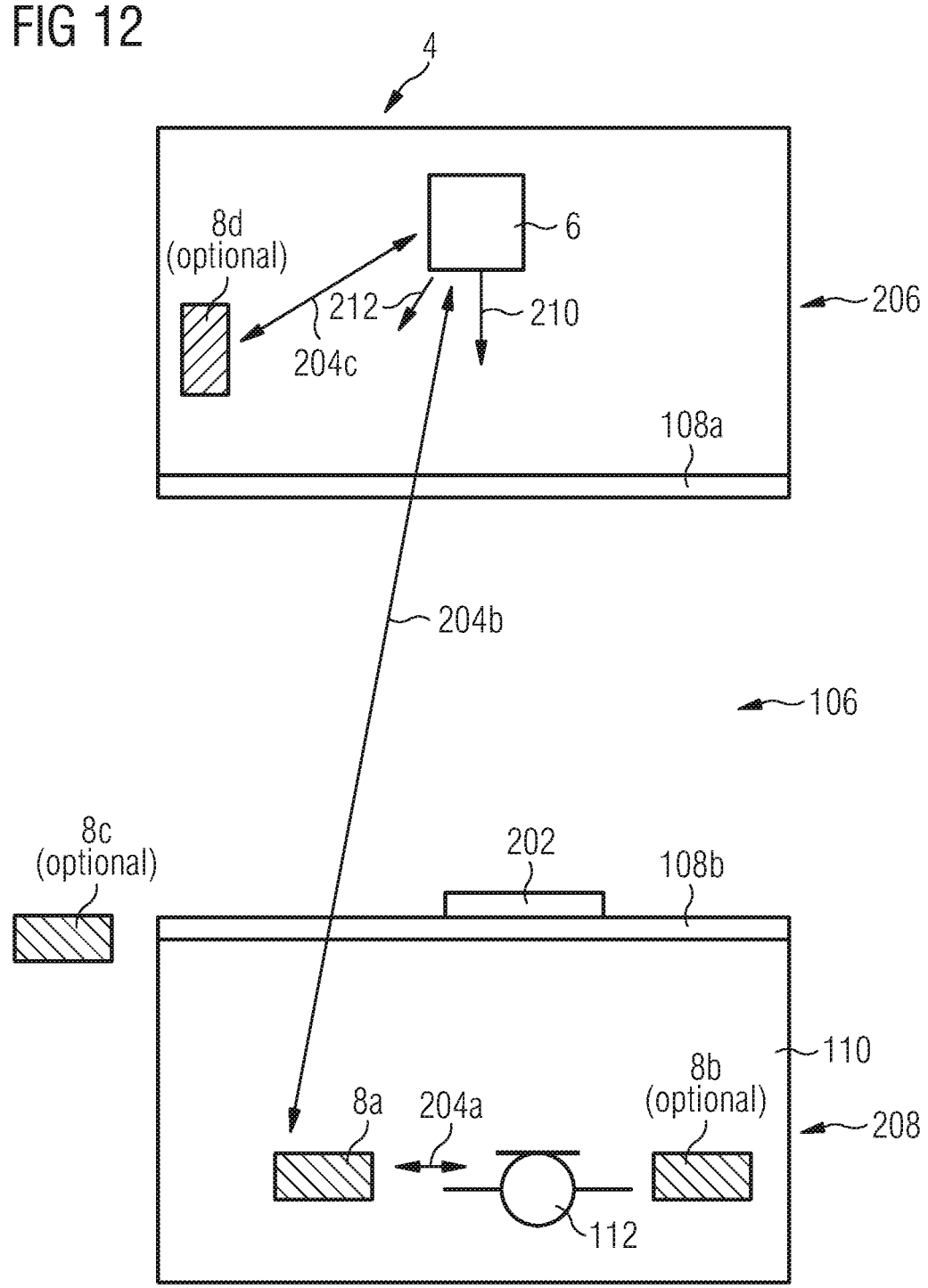
FIG. 12 shows a schematic cross sectional view of an exemplary photoacoustic sensor according to one or more embodiments.

In the following, embodiments of the invention will be described in further detail. Elements shown in the respective figures having the same or a similar functionality will have associated therewith the same reference signs.

FIG. 1 shows a schematic block diagram of an apparatus 2 for in-situ calibration of a photoacoustic sensor 4 e.g. achieved with adjusting an IR emitter 6 according to a first aspect. The apparatus 2 comprises a measurement device 8 and a calibration unit 10. The measurement device is configured to detect a current electric signal (or instantaneous electrical signal) 7 at the IR emitter of the photoacoustic sensor and to provide the calibration unit 10 with an information signal 9 based on the detected current electric signal 7. A current electric signal is, for example, a voltage at or over the IR emitter, an electrical current through the IR emitter, or an input power of the IR emitter. Moreover, the IR emitter may be a heating wire, a LED or a laser. The calibration unit 10 is configured to compare the detected current electric signal at the IR emitter with a comparison value for the electric signal to achieve a comparison result 11 forming a calibration information. When performing the in-situ calibration, the calibration information (or the comparison result) 11 is applicable to the photoacoustic sensor for adjusting the IR emitter and/or is applicable to an output signal 17 of the photoacoustic sensor for correcting the output signal 17.

According to embodiments, the calibration unit 10 may then adjust the current electric signal based on the comparison result 11 (calibration information) to obtain a target value of the electric signal at the IR emitter to perform the in-situ calibration. Again, the electric signal may be an electric current, a voltage at the IR emitter, or a combination thereof, for example an electric (input) power or a resistance of the IR emitter, or may be derived therefrom.

According to further embodiments, the photoacoustic sensor may optionally comprise a processing unit 15. The processing unit 15 may process the output signal of the photoacoustic sensor based on the calibration information to obtain an adjusted output signal of the photoacoustic sensor 4. The output signal of the photoacoustic sensor may be a response of an acoustic sensor element such as a microphone of the photoacoustic sensor to the photoacoustic signal caused by the IR radiation of the IR emitter to a gas concentration of a gas component of the measurement gas or a composition of the measurement gas. However, the calibration information may be provided to the IR emitter or to the processing unit or to both, the IR emitter and the processing unit. In other words, a direct adjustment of the IR emitter may perform an adjustment of the IR radiation of the IR emitter, wherein an indirect adjustment may calculate a calibration value based on e.g. a deviation of the (current) IR radiation (measure) to a calibrated IR radiation (measure), e.g. using a lookup table, to adjust the output signal of the photoacoustic sensor. Moreover, the processing unit 15 and the calibration unit 10 may be implemented in the same or a common (micro-) processor. In other words, the calibration unit 10 and the processing unit 15 may be implemented or incorporated in (the same) hardware and/or software or at least partially in hardware. Furthermore, the calibration information 11 may be input to the IR emitter 6 or the processing unit 15, dependent on the embodiment.

In other words, a current electric current, voltage, power, or resistance of the IR emitter may be measured using the measurement device 8 and be compared to a target value of the measured electrical property. Furthermore, the power source may be adjusted such that the current physical property or electric signal and the (expected) target value converge. In other words, an absolute difference of (a value of) the current physical property and (a value of) the target value of the physical property may be reduced. A convergence of the current electric signal and a target value of the electric signal is advantageous or may be even necessary to emit a target value or a physical characteristic from the IR emitter. The physical characteristic may be a temperature or an IR radiation of the IR emitter. In other words, the IR emitter itself may be sensor indicating a degradation of the emitter e.g. by a change of resistance. The resistance of the IR emitter suffering from degradation may change differently over the temperature when compared to a calibrated or known temperature range.

Moreover, adjusting the IR emitter or the output signal may refer to a calibration. Therefore, the adjustment may reduce a difference or an error between a current signal having an electromagnetic spectrum and a calibrated value of the electromagnetic spectrum. Accordingly, a difference or an error between a current output signal and a calibrated value of the output signal (as a response to the electromagnetic waves transmitted or emitted by the IR emitter) is reduced. This may refer to a calibrated IR emitter or a calibrated output signal.

FIG. 2 shows a schematic block diagram of an apparatus 2' for in-situ calibration of a photoacoustic sensor 4 e.g. achieved with adjusting an IR emitter 6 according to a second aspect. The apparatus 2' comprises again a calibration unit 10 and a sensing unit 8'. However, the calibration unit is configured to control a signal generator 12 such that the signal generator feeds an IR emitter of the photoacoustic sensor with an electric pulse 13, e.g. a pulse signal or pulsed signal. The sensing unit 8' is therefore configured to detect a current physical characteristic 7' of a surface of the IR emitter, wherein the current physical characteristic of the IR emitter depends on the electric pulse. The physical characteristic may be a temperature at the surface of the IR emitter or an emissivity of, for example, an IR radiation, a temperature radiation or a further electromechanical radiation. The sensing unit 8' may be configured to detect or measure the physical characteristic and therefore be capable of measuring a temperature, electromechanical waves or IR radiation. This may be a temperature sensor, a bolometer, or an IR diode, to name only a few examples, and to provide the calibration unit 10' with an information signal 9' based on the detected physical characteristic 7'.

Moreover, the calibration unit 10' is configured to compare the (detected) current physical characteristic of the surface of the IR emitter with a target value of the physical characteristic of the surface of the IR emitter to obtain a calibration signal 11' forming a calibration information. When performing the in-situ calibration, the calibration information is applicable to the signal generator (12) for adjusting the IR emitter and/or is applicable to an output signal of the photoacoustic sensor for correcting the output signal.

According to embodiments, the calibration unit may adjust the electric pulse 13 of the signal generator 12 based on the calibration signal to perform the in-situ calibration. In other words, the calibration unit determines the physical characteristic at the surface of the IR emitter, wherein the calibration unit compares this value with a target value of the physical characteristic. The target value of the physical characteristic may be a current temperature or IR radiation used for performing a gas concentration measurement. However, the calibration unit may adjust the signal generator, for example a total power or a modulation frequency of an electric signal, such that the target value or the expected value of the physical characteristic is obtained at the surface of the IR emitter.

According to further embodiments, the apparatus 2' may optionally comprise a processing unit 15 configured to process an output signal of the photoacoustic sensor based on the calibration information to obtain an adjusted output signal of the photoacoustic sensor. The output signal of the photoacoustic sensor may be a response of an acoustic sensor element of the photoacoustic sensor to the IR radiation of the IR emitter or a gas concentration of a gas component of the measurement gas or a composition of the measurement gas. However, the calibration information may be provided to the IR emitter or to the processing unit or to both, the IR emitter and the processing unit. In other words, a direct adjustment of the IR emitter may perform an adjustment of the IR radiation of the IR emitter, wherein an indirect adjustment may calculate a calibration value based on e.g. a deviation of the (current) IR radiation (measure) to a calibrated IR radiation (measure), e.g. using a lookup table, to adjust the output signal of the photoacoustic sensor. Moreover, the processing unit 15 and the calibration unit 10 may be implemented in the same or a common (micro-) processor (or in software) or at least partially in hardware.

The measurement device 8 (e.g. shown in FIG. 1) and the sensing unit 8' (e.g. shown in FIG. 2) are mutually applicable blocks within all related embodiments. However, the term measurement device may imply measuring, for example a voltage, an electric current, a resistance, or an electric (input) power, wherein sensing unit may refer to sensors such as, for example temperature sensors or IR sensors detecting or measuring e.g. an (output) power of the IR emitter. Nonetheless, since the electrical properties and the temperature or radiation properties are directly related to each other through the IR emitter there is a good reason to perform a switching of the aforementioned blocks 8 and 8'. Furthermore, apparatus 2 and apparatus 2' are mutually applicable as well.

FIG. 3 shows a schematic functional block diagram of both aforementioned aspects according to embodiments. Even though, it is adapted to the first aspect described with respect to FIG. 1 at the first sight, it may easily be adapted to the second aspect by removing the electrical connections 14 between the IR emitter 6 and the measurement device 8 (since the sensing unit may detect a temperature or an IR radiation of the IR emitter). However, when referring to the first aspect, the measurement device 8 below the IR remitter and connected in parallel to the IR emitter may be, for example a voltmeter. Additionally or alternatively, the measurement device 8 may be connected in series to the IR emitter 6 if it is, for example, an ampere-meter or ammeter. Furthermore, the calibration unit 10 receives a measurement result 9 from the measurement device 8 and may calculate a current electrical power at the IR emitter 6 or a current resistance of the IR emitter 6. Moreover, the calibration unit 10 may send a signal 16 to the signal generator 12 or power source 12, such that an output of the power source 12 is adjusted such that for example a target power input to the IR emitter 6 is achieved. Therefore, the calibration unit 10 may be configured to adjust the current electric signal (e.g. the feed or control signal) 18 such that a change of resistance of the IR emitter 6 is compensated. The change of resistance of the IR emitter may be due to a change of the mechanical properties of the IR emitter, for example due to the high temperatures the IR emitter is subjected to. In other words, the high temperatures of the IR emitter may cause an early degradation of the IR emitter. However, other influences may also cause a degradation of the IR emitter 6.

As already mentioned, power source 12 may be either configured to provide a regular AC or DC power to the IR emitter 6 to perform gas concentration measurements with the photoacoustic sensor during normal operation modes. Moreover, the power source 12 may also be configured to function as a signal generator being able to provide more sophisticated voltages or forms of the electrical current such as, for example, Dirac pulses, rectangular pulses, or step functions. According to further embodiments, the power source or signal generator 12 may be formed in two separate blocks for the signal generation and the power supply for the IR emitter 6.

Furthermore, the current electrical signal 18 may comprise an electric pulse, e.g. a pulse signal or pulsed signal. The electric pulse may be either part of normal operation of the photoacoustic sensor or it may only be applied for calibration purposes during a separate calibration measurement. However, the calibration unit 10 may be configured to calculate a time constant of the photoacoustic sensor from the current physical characteristic based on the electric pulse. The time constant may indicate an ability of the current physical characteristic to follow or track the electric pulse. Moreover, the calibration unit may adjust the electric pulse such that at least one of an edge steepness, an amplitude, or a repetition frequency of the electric pulse is changed and wherein the change of the electric pulse may change the physical characteristic of the IR emitter such that the absolute difference between a current physical characteristic and the target value of the physical characteristic is reduced. However, a difference between the target value of the physical characteristic and a current value of the physical characteristic may be obtained due to a degradation of the IR emitter.

The time constant or a further characteristical property may be, for example, obtained by evaluating a step function, a Dirac impulse, or a rectangular function. The time constant may therefore be a general measure characterizing the emitter performance not only for the currently applied electrical power but for a broad range of operating points such as, for example, all possible operating points of the photoacoustic sensor.

As already described, FIG. 3 may be already adapted to the second aspect described with respect to FIG. 2. Therefore, the sensing unit 8', replacing the measurement device 8, may be configured to measure a temperature of the surface of the IR emitter using, for example, determining a temperature of an environment of the IR emitter or by measuring an infrared radiation of the IR emitter at the surface of the IR emitter. Measuring a temperature of the environment of the IR emitter, such as for example measuring a temperature of a surrounding gas of the IR emitter may be referred to as an indirect measurement of a temperature of the surface of the IR emitter. Additionally or alternatively, the sensing unit 8' may be for example a radiation detector such as for example an IR detector or a bolometer, which may be referred to as a direct measurement. The radiation sensor may be configured to detect or measure, for example, an emissivity of the surface of the IR emitter, such as an emissivity of an IR radiation. Since the electric pulse is applied to the IR emitter, the sensing unit or sensing element may measure or detect a transient performance of the IR emitter. The transient performance of the IR emitter as a function of the input power depends (mainly) on the heat transfer or thermal transfer at the surface of the IR emitter. However, the transient performance may be the adaptation of an output power or performance to an input power or performance. A change or an error at the IR emitter may therefore be detected by comparing a current transient performance to a stored or target performance.

This method or operation is especially advantageous for fast photoacoustic sensors based on MEMS components.

These sensors may be small and therefore fast, since they comprise a small thermal mass when compared to bigger or larger sensors. However, if the surface of the IR emitter changes, which is for example a change of the material properties, such as for example a corrosion or oxidation of the surface, may result, for example in an offset or a time delay of an IR radiation. Additionally or alternatively, an overall drop of the temperature or an IR radiation of the IR emitter may be also caused.

According to further embodiments, a temperature of the IR emitter may be measured using a temperature sensor such as for example a PT element, a pn-diode, or a bolometer, etc., which may be integrated in the emitter or placed nearby the emitter. Comparing an input power of the IR emitter to an achieved temperature at the IR emitter reveals information regarding the emitter performance and may be used to adapt the input power to achieve a target value of the temperature. This may result in a constant IR emission. This embodiment and all other embodiments using a normal or an ordinary measurement signal, which may be also used to perform a gas concentration measurement of the PAS sensor, may be performed during normal operation of the photoacoustic sensor or during a separate calibration measurement.

According to further embodiments, a measurement signal of an acoustic sensor element of the photoacoustic sensor depends on an excitation frequency of the IR emitter. A change of the excitation frequency or an error of the IR emitter may be obtained by comparing the measurement signal to a stored reference signal. According to further embodiments, a transient behavior as well as an absolute value of a measurement signal of the gas concentration depends on or is based on a pressure of a reference cell. Comparing this transient behavior or performance, for example, with a stored performance, for example stored in an EEPROM or a further storage medium, may indicate a change of a pressure in the reference cell. This may provide information for a calibration or an error detection within the pressure measurement module or the reference cell.

According to further embodiments a variation of the temperature of the IR emitter results in a change of an emitted IR spectrum or a shift or offset of the spectrum. Therefore, by changing the emitter temperature a sensitivity of the photoacoustic sensor may be achieved for different gases, which may result in an adjustable sensitivity of the PAS sensor. A regular (periodic) comparison with a stored behavior reveals information about a composition of a current measurement gas, for example in a long-term measurement, or reveals information of a change of the sensor characteristics or an error in the PAS sensor, for example when evaluating a short-term profile.

According to further embodiments, a transient behavior and an achieved temperature of the emitter depends on a composition of the surrounding gases, for example of a (atmospheric) humidity. Periodically comparing the measured transient behavior to a stored transient behavior reveals information of a composition of the gases, for example sealing gases of the IR emitter and/or the acoustic sensor element of the photoacoustic sensor, if, for example, evaluating a long-term behavior. Moreover, it may reveal information about a change of the properties or characteristics of the photoacoustic sensor if for example evaluating a short-term behavior. A change of, for example a sealing gas of the IR emitter may influence the heating performance of the IR emitter. It may be seen that for example a humidity or a composition of gases may change comparably slow, which may be measured or detected in a long-term measurement or long-term behavior, wherein a degradation of the emitter may be comparably fast or even performed by a jump-up or by a sharp rise, which may be measured in a short-term behavior or short-term measurement of the photoacoustic sensor.

Embodiments relate to an in-use, online, or in-situ calibration of PAS-sensors comprising error detection or detection of cross-sensitivities, for example by a change of a sealing gas composition, which affects the measurement or detection of gas concentrations of a measurement gas. Therefore, a temperature sensor may measure an IR emitter temperature and compare the measured temperature to a target value or a stored value with respect to (or considering) an input power to the IR emitter. The temperature sensor may be, for example, a PT wire which may be used both as the IR emitter (or heater) and the temperature sensor. This may relate to both, a typical AC or DC behavior or a transient behavior. Moreover, a transient behavior of a gas sensor measurement unit (i.e. the acoustic sensor element) of the photoacoustic sensor may be obtained and, for example, compared with a stored behavior. This may be achieved by a variation of the IR radiation by changing the input power to the IR emitter, analyzing the resulting measurement signal and comparing characteristic absorption curves of different gases. This may be achieved using for example the upcoming embodiments of the third aspect.

To be more specific, according to embodiments an in-situ or in use calibration of the photoacoustic sensor 4 may be performed based on the calibration information 20 which may be derived from a physical parameter or characteristic of the photoacoustic sensor or, for example, of the IR emitter 6 of the photoacoustic sensor, and which are achieved or detected during operation of the photoacoustic sensor or the IR emitter, respectively.

The sensing unit may be configured to detect or measure the physical characteristic of the IR emitter and to provide the calibration unit with measurement signals (or an information signal) based on the detected physical characteristic. The sensing unit may be part of the photoacoustic sensor for directly sensing the physical parameter or, alternatively, may be arranged external to the photoacoustic sensor for indirectly sensing the physical parameter.

The in-situ calibration of the photoacoustic sensor may be conducted by adjusting the IR emitter based on the calibration information, e.g. by adjusting a control signal fed to the IR emitter and/or by correcting the output signal of the IR emitter (or a signal derived from the output signal). Moreover, the in-situ calibration of a photoacoustic sensor may be conducted during processing or evaluating the output signal of the IR emitter (or a signal derived from the output signal), wherein the detected calibration information is incorporated into the processing or evaluating of the output signal of the IR emitter (or a signal derived from the output signal). As a result, a corrected processing or evaluating of the output signal of the IR emitter (or a signal derived from the output signal) can be conducted. Therefore, a calibrated measurement signal may be achieved.

FIG. 4 shows a schematic block diagram of an apparatus 2" for in-situ calibration of a photoacoustic sensor 4 according to a third aspect according to embodiments. The apparatus 2" comprises a calibration unit 10 configured to calculate a calibration information 20. The IR emitter 6 of the photoacoustic sensor 4 is furthermore configured to emit an electromagnetic spectrum (e.g. an electromagnetic signal or electromagnetic radiation having an electromagnetic spectrum), wherein the photoacoustic sensor, or more specifically, an acoustic sensor element of the photoacoustic sensor may be configured to provide at least two measurement signals 22 based on at least two electromagnetic spectra, wherein the calibration unit 10 may be configured to compare the at least two measurement signals 22 to obtain the calibration information 20. The acoustic sensor element may be different from the sensing element and is configured to receive the electromagnetic wave(s) emitted or send out by the IR emitter. Moreover, the calibration unit 10 may be configured to apply the calibration information 20 (directly) to the photoacoustic sensor (or to an output signal of the photoacoustic sensor) to perform the in-situ calibration. According to further embodiments, the calibration unit may be configured to control an electric signal at the IR emitter, such as for example an electric power of the IR emitter. Moreover, the IR emitter may emit an electromagnetic spectrum based on the electric signal and the calibration unit may be further configured to adjust the electric signal at the IR emitter based on the calibration information 20 to perform the in-situ calibration. The calibration information 11, 11' and 20 are mutually applicable.

In the following, some exemplary calibration concepts are described in the context of the embodiments of FIG. 4.

An acoustic sensor (element) of the photoacoustic sensor may receive an acoustic signal from a measurement gas, which may be excited by an (alternating or modulated) electromagnetic spectrum or signal. The calibration unit performs an iteration or analysis of the measurement signals 22 and compares the measurement signals to each other. Optionally, the calibration unit 10 compares the measurement signals to a stored reference if, for example the current reference gas composition is known. These may be options to derive the calibration information. However according to a preferred embodiment, the calibration unit may adjust the input of the IR emitter based on the calibration information such that a target IR radiation or temperature of the IR emitter is obtained if the calibration information reveals that a current performance of the IR emitter changed compared to an initial calibration or a previous calibration.

Additionally or alternatively, to adjust the input power of the IR emitter, it may be further changed a mapping or a transformation of the measurement signal to a respective gas concentration in the measurement gas, for example by adjusting a lookup table based on the calibration information. In other words, the calibration unit 10 may be configured to calibrate a determination of gas concentration in the photoacoustic sensor using the calibration information to perform the in-situ calibration. The determination of the gas concentration may be based on a further measurement signal of the photoacoustic sensor. The further measurement signal may be derived using settings of the IR emitter that are different from the settings applied for measuring the (first or previous) measurement signal. A different setting may refer to different temperatures, different IR radiation or in general, electromagnetic radiation, e.g. induced by a change of the electrical current, voltage, or input power.

In other words, the calibration unit 10 may be configured to calculate a current ratio of a first of the at least two measurement signals and a second of the at least two measurement signals, wherein the calibration unit is further configured to compare the current ratio to a target ratio. However, the first and the second of the at least two measurement signals may be derived using settings of the IR emitter for the first of the at least two measurement signals that are different from the settings applied for measuring the second of the at least two measurement signals.

According to further embodiments, the apparatus 2" may optionally comprise a processing unit 15, which may be configured to adjust the electric power such that an absolute difference of the current ratio to the target ratio is reduced, or the calibration unit may be configured to calibrate a determination of a gas concentration in the photoacoustic sensor such that the absolute difference of the current ratio to the target ratio is reduced.

In other words, a drift of the spectrum, e.g. due to a change of the emissivity of the emitter, may be applied or forced and further calibrated through a change of the temperature of the emitter. Therefore, having a current operating point that is slowly or even not changing or drifting, e.g. the operating point being sensitive to an absorption spectrum of a slowly or even not changing gas (composition), a comparison of one or more operating points may indicate a degradation or even an amount of degradation of the IR emitter. An operating point is e.g. measurement using a current temperature or IR radiation of the IR emitter.

Moreover, the processing unit may be configured to process an output signal 17 of the photoacoustic sensor based on the calibration information to obtain an adjusted output signal of the photoacoustic sensor. The output signal of the photoacoustic sensor may be a response of an acoustic sensor element of the photoacoustic sensor to the IR radiation of the IR emitter or a gas concentration of a gas component of the measurement gas or a composition of the measurement gas. However, the calibration information may be provided to the IR emitter or to the processing unit or to both, the IR emitter and the processing unit. In other words, a direct adjustment of the IR emitter may perform an adjustment of the IR radiation of the IR emitter, wherein an indirect adjustment may calculate a calibration value based on e.g. a deviation of the (current) IR radiation (measure) to a calibrated IR radiation (measure), e.g. using a lookup table, to adjust the output signal of the photoacoustic sensor. Moreover, the processing unit 15 and the calibration unit 10 may be implemented in the same or a common (micro-) processor.

The in-situ calibration of the photoacoustic sensor may be conducted by adjusting the IR emitter based on the calibration information, e.g. by adjusting a control signal fed to the IR emitter and/or by correcting the output signal of the IR emitter (or a signal derived from the output signal). Moreover, the in-situ calibration of a photoacoustic sensor may be conducted during processing or evaluating the output signal of the IR emitter (or a signal derived from the output signal), wherein the detected calibration information is incorporated into the processing or evaluating of the output signal of the IR emitter (or a signal derived from the output signal). As a result, a corrected processing or evaluating of the output signal of the IR emitter (or a signal derived from the output signal) can be conducted.

More specifically, a first of the at least two measurement signals may be derived using a spectrum, which is sensitive to the current measurement gas. As a reference, a second measurement signal of the at least two measurement signals may be obtained using a spectrum, which is not sensitive to the current measurement gas. A difference of the second measurement signal (reference measure) to a reference measure obtained during calibration of the photoacoustic sensor may result in the calibration information, which may be applied to the first measurement signal. For example, the first measurement signal may be increased or decreased by the difference obtained from the reference measure. In other words, the calibration information is the difference obtained from the reference measure or a measure of the difference obtained from the reference measure.

Furthermore, an intensity of the IR radiation of the IR emitter may be derived from an alternating sequence of the at least two measurement signals, obtained from an alternating sequence of two electromagnetic spectra (e.g. IR spectra). The two electromagnetic spectra may be chopped or iteratively alternated using a (chopping) frequency which may be (e.g. at least 10 times) higher than a (average) change of the composition of the measurement gas. In other words, from two different sensitivities of the acoustic sensor element of the photoacoustic sensor, related to two different electromagnetic spectra, the (current) intensity of the IR emitter may be derived.

FIG. 5 shows a schematic block diagram of a micromechanical system 100 according to embodiments, optionally comprising the photoacoustic sensor 4. The micromechanical system 100 may comprise multiple (wafers of a) semiconductor substrate(s) 102, such as for example six semiconductor substrates 102a-102f as depicted in FIG. 5. Semiconductor substrates 102a-102c may form a wafer stack of an acoustic sensor element of the photoacoustic sensor and furthermore, semiconductor substrates 102d-102f may form an emitter of the photoacoustic sensor, wherein the IR emitter 6 is part of the emitter. Together with the cavities 104a and 104b, the IR emitter 6 may form a black body radiator. A further cavity 106 may house a measurement gas whose components will be analyzed by the photoacoustic sensor. Therefore, the IR emitter 6 may transmit IR radiation through the housing 108a,b of the measuring chamber 106, which is permeable or invisible for IR radiation. The measuring gas within measuring chamber 106 may absorb specific wavelengths of the IR radiation due to the photoacoustic effect. The reduced IR radiation spectrum further strikes on a reference gas or stimulates the reference gas within reference chamber 110 and is again stimulated due to the photoacoustic effect. A membrane, sensor, or microphone 112 may measure the stimulation or excitation of the reference gas and provide a measurement signal 22.

Since the whole photoacoustic sensor 4 may be implemented in one or more semiconductor substrates, it may be advantageous to also include the apparatus 2, 2', or 2" (which are mutually applicable) in one of the semiconductor substrates used to form the photoacoustic sensor. This may reduce a construction size of the overall microelectromechanical system 100. It is further advantageous to integrate the apparatus into the photoacoustic sensor, since the measurement device or the sensing unit 8, 8' may be easily formed within the semiconductor substrate, for example using a pn junction, a thermopile or a (temperature depending) resistor. In other words, the micromechanical system 100 may comprise an apparatus and the IR emitter, wherein the apparatus and the IR emitter of the photoacoustic sensor are formed in a common semiconductor substrate, and wherein the sensing unit or sensing element 8' or measurement device 8 comprises a semiconductor sensing unit formed within the semiconductor substrate. A semiconductor sensing unit may be a semiconductor temperature sensing unit or a semiconductor IR sensing unit. In other words, the semiconductor sensing unit may be formed or integrated in the semiconductor substrate. However, the description regarding the sensing units also applies mutatis mutandis or analogously.

Moreover, the described photoacoustic sensor 4 comprising a wafer stack of multiple wafers 102 may use or provide a chopper or modulation frequency within 1 to 100 Hz and a comparably small heat or thermal capacity. The modulation of the IR emitter may be performed using a change of an amplitude of the input signal or a change of the frequency of the input signal of the IR emitter. Therefore, the IR emitter may be operated using pulse-width modulation, amplitude modulation, or pulse-density modulation.

Moreover, an integrated apparatus 2, 2', 2", wherein the apparatus and the photoacoustic sensor are integrated in one or more common semiconductor substrates to form a microelectromechanical system. Such a microelectromechanical system are small systems having and enabling high duty cycles due to a low heat or thermal capacity. Moreover, multigas sensors may be formed e.g. by forming an array of these microelectromechanical systems having different (IR) excitation frequencies, or using different (IR) excitation frequencies in one microelectromechanical system, e.g. one after the other. Again, the small heat capacity resulting in a fast cool down of the IR emitter enables the system driving different excitation frequencies in a rapid succession.

In the following, multiple methods will be described which may be performed by one or more of the previously described aspects.

FIG. 6 shows a schematic block diagram of a method 600 which may be performed by aspect 1. In a step 605, an IR emitter target or multiple IR emitter targets comprising a power (I, U) and a temperature are derived, calculated or set. In other words, it may be fed a lookup table with pairs of a (input) power (or an electrical current and an electrical voltage) and a corresponding temperature. During calibration mode or during normal operation, an IR emitter resistance is measured in a step 610. In a step 615, a calibrated IR emitter resistance is derived from a calibrated temperature dependency, e.g. the lookup table of step 605, using a current input power of the IR. In a step 620, the IR emitter resistance of the measurement and the calibrated value is compared. Based on the comparing, in a step 625, an adapted power is calculated to keep the temperature on target. The adapted power input of step 625 is further input to IR emitter 6 in a step 630.

FIG. 7 shows a schematic block diagram of a method 700, which may be advantageously performed using aspect 2 of the aforementioned aspects. In a step 705, the IR emitter target is defined using a transient behavior of the (output) power or the resistor (IR emitter) as a function of the form of the input signal. The transient behavior of the resistor may be seen as a transient behavior of the resistance of the IR emitter, or according to preferred embodiments, as an ability of the IR emitter to transform the input power to an output power (efficiency of the IR emitter), derived using measuring the temperature of the environment of the IR emitter or an IR radiation of the IR emitter. The transient behavior of the resistance may indicate a change or an alteration or a degradation of a surface of the IR emitter, since load carriers such as electrons become distributed near the surface of the IR emitter due to the skin effect. The skin effect is the tendency of an alternating electric current (AC) to become distributed within a conductor such that the current density is largest near the surface of the conductor, and decreases with greater depths in the conductor. The electric current flows mainly at the "skin" of the conductor, between the outer surface and a level called the skin depth. The skin effect causes the effective resistance of the conductor to increase at higher frequencies where the skin depth is smaller, thus reducing the effective cross-section of the conductor. The skin effect is due to opposing eddy currents induced by the changing magnetic field resulting from the alternating current.

During operation of the IR emitter 6, in a step 710 a transient behavior of the power/resistor is measured. Accordingly, a transient behavior of the power/resistor is derived from the calibrated temperature dependency based on the current power input of the IR emitter in a step 715. In a step 720, the transient behavior of the power/resistor of the measurement and the calibrated value is compared. Furthermore, in a step 725, an adapted (input) power of the IR emitter or an adapted form of the input signal to the IR emitter 6 is calculated to keep the temperature/form on target, wherein in a step 730 the calculated power or form of the input signal is applied to the IR emitter 6. The method 700 may perform a control or calibration of the IR emitter based on a transient behavior.

FIG. 8 shows a schematic block diagram of a method 800 which may control or calibrate the IR emitter based on a (transient) behavior of the detector signal. Method 800 comprises a step 805, wherein IR emitter target is defined as a transient behavior of the detector as a function of the form of the input signal. Again, as already seen with respect to methods 600 and 700, in a step 820, a transient behavior of the detector is compared using the measurement signal derived in a step 810 and a calibrated value derived in a step 815, wherein the transient behavior of the detector depends, for example on the calibrated temperature or form, or on a concentration dependency of the measurement signal to the concentration of the (measurement or reference) gas. Moreover, in a step 825 an adapted power or form of the input signal of the IR emitter is calculated to keep the temperature or form of the input signal on target and in a step 830 the calculated input signal is adapted to the IR emitter 6. The method 800 may be advantageously performed by aspect 3.

FIG. 9 shows a schematic block diagram of a method 900 for performing an in-situ calibration of a photoacoustic sensor 2 with adjusting an IR emitter. The method 900 comprises measuring a current electric signal at the IR emitter of the photoacoustic sensor in a step 905 and comparing the current electric signal at the IR emitter with a comparison value for the electric signal to achieve a comparison result forming a calibration information and wherein, when performing the in-situ calibration, the calibration information is applicable to the photoacoustic sensor for adjusting the IR emitter and/or is applicable to an output signal of the photoacoustic sensor for correcting the output signal in a step 910.

FIG. 10 shows a schematic block diagram of a method 1000 for in-situ calibration of a photoacoustic sensor achieved with adjusting an IR emitter. The method 1000 comprises a step 1005 of controlling a signal generator such that the signal generator feeds an IR emitter of the photoacoustic sensor with an electric pulse or pulse(d) signal, a step 1010 of detecting a current physical characteristic of a surface of the IR emitter, wherein the current physical characteristic of the IR emitter depends on the electric pulse, and a step 1015 of comparing the current physical characteristic of the surface of the IR emitter with a target value of the physical characteristic of the surface of the IR emitter to obtain a calibration signal forming a calibration information wherein, when performing the in-situ calibration, the calibration information is applicable to the signal generator for adjusting the IR emitter and/or is applicable to an output signal of the photoacoustic sensor for correcting the output signal.

FIG. 11 shows a method 1100 for in-situ calibration of a photoacoustic sensor. The method 1100 comprises a step 1105 of calculating a calibration information, wherein an IR emitter of the photoacoustic sensor is configured to emit an electromagnetic spectrum based on the electric signal, wherein the photoacoustic sensor is configured to provide at least two measurement signals based on at least two electromagnetic spectra, and a step 1110 of comparing the at least two measurement signals to obtain a calibration information, and to apply the calibration information to the photoacoustic sensor to perform the in-situ calibration.

FIG. 12 shows a schematic cross sectional view of an exemplary photoacoustic sensor according to embodiments. The photoacoustic sensor may be part of or connected to the apparatus 2', 2" for in-situ calibration of a photoacoustic sensor 4. Thus, apparatus-specific features such as e.g. the signal generator 12 or the calibration signal 11' are not explicitly shown in FIG. 12. However, these features may be applied accordingly to the embodiments described with respect to FIG. 12. The features are described e.g. in FIG. 2.

The apparatus 2' for in-situ calibration of a photoacoustic sensor 4 comprises a light emitter 6, an acoustic sensor element 112, a sensing unit 8a and a calibration unit 10. The light emitter may emit light along a transmission path 210 to a gas which may be a measurement gas. The acoustic sensor element 112 may detect an acoustic signal emitted from the gas based on the received light. In other words, the acoustic signal, also referred to as photoacoustic signal, is caused by the emitted light that affects the gas. The sensing unit 8a may detect the light transmitted along the transmission path 6 and provides an output signal. The calibration unit receives the output signal from the sensing unit 8a and provides a calibration information based on the output signal from the sensing unit 8a. The calibration information may be used to in-situ calibrate the photoacoustic sensor.

The photoacoustic sensor may comprise sensing units 8a, 8b, 8c, 8d in the regular light transmission path used to determine physical characteristics of the IR emitter or the acoustic sensor element 112 of the photoacoustic sensor. The resulting output signals of the sensing units may be used to determine a difference between an expected physical characteristics determined using a calibrated photoacoustic sensor and the current physical characteristics. Thus, based on the difference, the photoacoustic sensor may be in-situ (e.g. during regular operation of the photoacoustic sensor without affecting the operation) recalibrated, e.g. by minimizing the difference due to adjusting the IR emitter and/or adapting an output signal of the photoacoustic sensor.

In other words, the apparatus 2', 2" comprises a calibration unit 10 configured to control a signal generator 12 (not shown in FIG. 12) such that the signal generator feeds the IR emitter with an electric signal. Furthermore, a sensing unit 8a is configured to detect a current physical characteristic of the IR emitter 6, wherein the current physical characteristic of the IR emitter depends on the electric signal. The calibration unit may compare the current physical characteristic of the IR emitter 6 with a target value of the physical characteristic of the IR emitter to obtain a calibration signal 11' (not shown in FIG. 12) forming a calibration information. When performing the in-situ calibration, the calibration information is applicable to the signal generator 12 for adjusting the IR emitter and/or is applicable to an output signal of the photoacoustic sensor for correcting the output signal. When applying the calibration information to the output signal, the correction may be performed in the sensing unit 8a or in a further evaluation unit such as an application-specific integrated circuit (ASIC) In other words, the calibration information may be applied to the acoustic sensor element 112 to output a corrected output signal even though the photoacoustic signal is affected e.g. by degradation.

According to embodiments, the calibration unit 10 may control the signal generator 12 such that the signal generator feeds the IR emitter with an electric pulse as the electric signal. In other words, the electric signal formed by the signal generator may be an electric pulse. To form the electric pulse, the apparatus 2', 2" may comprise a further optional sensing unit 8d configured to detect the current physical characteristic of the IR emitter 6, wherein the calibration unit comprises a threshold switch configured to signal the signal generator to stop feeding the IR emitter with the electric signal if the physical characteristic exceeds a threshold value. The physical characteristic describes e.g. an inbound radiation or (an emission spectrum of) light or a corresponding temperature that may be determined based on the detected light spectrum.

Therefore, the further sensing unit 8d may be located in close proximity, e.g. located in the same chamber as the IR emitter. A distance 204c between the further sensing unit 8d and the IR emitter 6 may be less than 0.5 times, less than 0.25 times, or less than 0.1 times a distance between the IR emitter 6 and the acoustic sensor element 112. The close proximity of the further sensing unit 8d to the IR emitter enables measuring the physical characteristic of the IR emitter with high precision.

Furthermore, the threshold switch may comprise a hysteresis such that, when falling behind a further threshold value, the signal generator starts feeding the IR emitter with the electric signal. In other words, the threshold switch may be (electrically) connected to the further sensing unit 8d, which may be a photodiode or a temperature sensor. If the (predetermined) threshold of a brightness or temperature of the IR emitter is reached, the IR emitter may be stopped heating. The regular measurement and/or the calibration measurement may therefore be performed using a constant emitted power or constant emitted spectrum of the IR emitter. According to one embodiment, the photoacoustic sensor may be operated in a pulse mode. In the pulse mode, the IR emitter is controlled such that the emitted intensity increases until a maximum value is reached and thereafter decreases until a minimum value is reached. Even when the photoacoustic sensor is operated in a pulse mode, the threshold switch allows to perform the calibration measurement at the same characteristic of the emitted light, e.g. same power or same frequency spectrum of the emitted light. To ensure that the same characteristic is used for the calibration, the calibration is triggered when the threshold switch reaches the threshold. The threshold switch may be a Schmitt-Trigger. However, additionally or instead of the further (lower) threshold value, a time-based restart of the heating of the IR emitter may be performed. Thus, the calibration unit may be configured to restart the heating of the IR emitter by applying the electric signal to the IR emitter.

The electric pulse may vary in terms of e.g. frequency spectrum of the light or IR radiation emitted by the IR emitter that may be caused due to providing a different input power to the IR emitter resulting in a different emitted spectrum for calibration and deterioration detection. E.g., if an input power of between 0.8 W and 1.2 W causes an emitted spectrum of a highest intensity between 5 µm and 7 µm, wherein a lower input power of between 0.3 W and 0.7 W may cause an emitted spectrum of a highest intensity between 2 µm and 4 µm.

Furthermore, using different signal pulses having different characteristics may enable differentiating between effects caused by changes of the characteristics within the measurement gas that may vary due to varying pressures, compositions or temperatures of the measurement gas, and influences which are not caused by the measurement gas such as effects due to the reference gas outside the measuring chamber or any polluted or degraded component. The different characteristics may for example include different repetition frequencies of the emitted light pulses (e.g. 10 Hz and 100 Hz repetition frequency), different emitted spectra of the emitted light pulses or different shapes of the emitted light pulses. Without any influence on the emitted IR spectrum of the IR emitter outside the measuring chamber, the photoacoustic signal generated by the emitted IR spectrum shows a known dependency on frequency and/or amplitude changes of the emitted IR signal. Thus, if the dependency between two different pulses differs from an expected dependency, e.g. if the dependency is non-linear rather than expected linear, it may be an indication that the photoacoustic sensor suffers e.g. from degradation and should be recalibrated. Using this technique, it is possible to even perform the in-situ calibration during regular measurements. Moreover, the frequency response of the acoustic sensor element 112 may be determined using different pulses of varying frequencies of the emitted IR spectrum. These pulses may be used for measuring as measuring pulses and/or for calibration as calibration pulses. Measurement signals or pulses may be referred to as primary signals wherein calibration signals or pulses may be referred to as secondary signals. Thus, according to embodiments, secondary signals may have the same characteristics and may be the same signals as the primary signals. In other embodiments, secondary signals may have different characteristics as primary signals.

According to embodiments, the at least one of the sensing units 8a, 8b, 8c, 8d may be dedicated to specific properties. For example, the sensing units 8a, 8b, 8c, 8d may be sensitive to a specific frequency or frequency range of the emitted IR or light spectrum. If any of the sensing units, when referring FIG. 12 any of the sensing units 8a and 8b, is located between the measuring chamber 106 and the acoustic sensor element 112, the sensing unit may for example detect a humidity in the measurement gas. Humidity may absorb a frequency component at a wavelength of 2.2 µm. Thus, a sensing unit sensitive to only wavelengths around 2.2 µm, e.g. between 2 µm and 2.5 µm, enables detecting an amount of humidity between the IR emitter and the sensing unit and/or in the measurement gas in the measuring chamber. This principle may be applied e.g. to gas mixtures where each gas component causes a specific frequency component in the photoacoustic signal.

According to embodiments, the sensing unit 8a is located at a first distance 204a to an acoustic sensor element 112 of the photoacoustic sensor and at a second distance 204b to the IR or light emitter 6 of the photoacoustic sensor, wherein the first distance is smaller than the second distance. In other words, the sensing unit 8a is located at a spatial position close to gas receiving the emitted light and converting to the emitted light to an acoustic signal The IR light reaching the sensing unit and the IR light reaching the gas are then both attenuated by substantially the same amount when compared to the physical characteristic at the IR emitter. An acoustic sensor element 112 for measuring the acoustic signal is arranged within the gas. In further other words, the sensing unit 8a may be located at a spatial position with respect to the acoustic sensor element 112 of the photoacoustic sensor such that the acoustic sensor element 112 and the sensing unit 8 share substantially the same effective transmission path of the emitted IR light.

In some embodiments, the acoustic sensor element 112 may be located in a reference chamber 110. In such embodiments, the acoustic sensor element 112 and the chamber in which the sensing unit 8 is located may share substantially the same effective transmission path of the emitted IR light.

By having the same effective transmission path of the emitted IR light, the sensing unit 8 is capable of measuring influences throughout the complete light transmission path used for the regular operation of the photoacoustic sensor. In embodiments, the length of both effective transmission paths may differ by not more than 5%, in other embodiments by not more than 10% and in still other embodiments by not more than 20%. The transmission path may be referred to as the shortest straight connection between the light emitter and the acoustic sensor element. Thus, refractions or optical shields affecting the transmitted light may be omitted.

In order to obtain the same effective transmission path, the sensing unit 8a is arranged in close proximity to the acoustic sensor element 112. This location of the sensing unit 8a in close proximity to the acoustic sensor element (microphone) 112 enables detecting multiple possible errors, changes, or alterations of the photoacoustic sensor which may occur in the transmission path, e.g. displacement of components within the transmission path, degradations of chamber windows or other optical elements due to dust or other particles etc. Distinguished from other concepts which monitor only the emitter or test only the acoustic sensor element 112, the described embodiments enable detecting degradation of all relevant components and takes them into account for calibration. The concept achieves this in a simple manner which requires only one sensing unit 8a at the end of the operative regular transmission path. However, optionally more than one sensing unit may be used.

According to some embodiments, the inner surfaces of the reference chamber 110 in which the acoustic sensor element 112 is placed may be coated with a reflecting material such as e.g. a gold coating. The reflecting coating enables reflections of the emitted light within the reference chamber 110 thus increasing the effective optical path of the signal emitted by the IR emitter. When using for example a pure reference gas in the reference chamber 110, this reference gas may serve as a natural filter where an increased effective optical path increases the effectivity of the filtering capabilities of the reference gas. Typically, photoacoustic sensors measure the purity of a measurement gas or a measurement gas composition. Thus a pure, i.e. an uncontaminated portion of the measurement gas or the measurement gas composition may be enclosed in the reference chamber surrounding the acoustic sensor element 112. Optical filters may be omitted.

Generally, the goal of calibrating the photoacoustic sensor is to control the stability or reliability of the photoacoustic sensor with all components. Hence, it is possible to detect changes within the complete transmission path or measurement path between the IR emitter and the acoustic sensor element 112 of the photoacoustic sensor. Changes or errors may be a degradation of the IR emitter, the surface of the IR emitter or (transparent) windows or transparent sealing 108a, 108b in the transmission path of the photoacoustic sensor element or misalignments of components. Furthermore, the windows may be polluted e.g. by dust, particles or due to condensation. Additionally, the photoacoustic sensor may be mechanically corrupted if e.g. a relative position of the IR emitter to the acoustic sensor element 112 is changed which may be caused by shocks during installation.

According to further embodiments, the apparatus 2', 2" comprises a further sensing unit 8d configured to detect the current physical characteristic of the IR emitter 6 at a position different from the position of the sensing unit. The further sensing unit 8d is located in a spatial position that is closer to the IR emitter when compared to a spatial position of the sensing unit 8a. In other words, the further sensing unit is located at a third distance 204c to the IR emitter, wherein the third distance is smaller than the second distance 204b. Furthermore, the embodiment is not limited to one further sensing unit. In some embodiments more than one further sensing units, such as sensing units 8c and 8d, may be placed at different positions in the photoacoustic sensor or nearby the photoacoustic sensor. The further sensing units 8c, 8d may be used to narrow a location or to locate the actual position of an error within the photoacoustic sensor. Thus, the sensing units may be located, in the view from the IR emitter, behind a respective component which may suffer from degradation or other changes during the lifecycle of the photoacoustic sensor. Thus, the further sensing units determine the physical characteristics of the IR light which is only partially attenuated (compared to the attenuation at the end of the transmission path) since the further sensing units are located between the sensing unit 8a and the IR emitter. Depending on the attenuation at the further sensing units, the deteriorated component of the photoacoustic sensor may be identified and compensated for. The amount of attenuation may be measured to directly estimate an amount of recalibration. The amount of recalibration may refer to a greater power of the electric signal or the electric pulse applied to the IR emitter and/or a degree of adaption of the output signal of the photoacoustic sensor. The adaption of the output signal enables to adjust the output signal such that the undesired attenuation is compensated.

According to embodiments, the calibration unit 10 is configured to determine which signal or signals should be adapted for calibration, based on a difference of the physical characteristic measured by the sensing unit 8a and the physical characteristic measured by the further sensing unit 8b, 8c, 8d. To be more specific, it can be determined whether to apply the calibration information for adjusting the IR emitter or to apply the calibration information to an output signal of the photoacoustic sensor for correcting the output signal. In other words, if the further sensing units identify the IR emitter as being suffering from degradation, the power of the electric signal may be readjusted to achieve a constant (maximum) brightness or temperature. However, if e.g. the windows are polluted, the output signal may be adjusted to avoid an adaption of the IR emitter resulting in higher temperatures and increased degradation or to avoid a change of the emitted (light) spectrum of the IR emitter.

In the described embodiments, the apparatus 2', 2", when performing the in-situ calibration, may use only signals from the same transmission path that are used to perform a regular measurement on a measurement gas. In other words, external signals are absent, such as e.g. signals from an acoustic generator for testing the acoustic sensor element. Therefore, the calibration information may be derived only from the physical characteristic of the IR emitter.

FIG. 12 reveals a measurement module 206 and a detector module 208. Exemplary, both modules are sealed with a transparent sealing 108a, 108b, respectively. However, this sealing is optional since the photoacoustic sensor may be used with open modules/chambers or with only one module being sealed and the other module remaining open. Hence, the embodiments described above with respect to FIG. 12 may be also applied to photoacoustic sensors with an open reference and/or measurement chamber, i.e. a reference/measurement chamber that is not sealed with the transparent sealing. An optical shield 202 may be applied in the optical path between the IR emitter and the acoustic sensor element/detector 112. Thus, the optical shield 202 shadows the detector 112.

Moreover, above have been described the sensing units 8a and 8d. FIG. 12 further reveals optional sensing units 8b and 8c which may be photodetectors or temperature sensors. The above described with respect to sensing unit 8a may also be applied to the sensing unit 8b. However, the sensing unit 8b may be outside the direct optical path of the IR signal wherein the sensing unit 8a may have a direct optical connection to the IR emitter. The optional further sensing unit 8c may be located outside the measurement chamber and the reference/detector chamber.

Thus, the further sensing unit 8c may detect the emitted light through a transmission path having a direction 212 different from a direction 210 of the transmission path. Thus, when referring to FIG. 12, the optical sensing unit may detect the emitted light that passes only the first transparent sealing 108a. In other words, the emitted light detected by the further sensing unit 8c omits passing the second transparent sealing 108b. This detected emitted light may suffer from attenuation due to a degradation of the light emitter or due to a degradation of the transparent sealing 108a. Hence, by determining a difference between the detected emitted light of the sensing unit 8a and the detected emitted light of the further sensing unit 8c, a degree of degradation of the second transparent sealing 108a may be obtained or at least estimated.

Further embodiments relate to the following examples:

1. Apparatus 2 for in-situ calibration of a photoacoustic sensor 4, the apparatus comprising: a measurement device 8 configured to measure a current electric signal 18 at the IR emitter 6 of the photoacoustic sensor 4; a calibration unit 10 configured to compare the current electric signal 18 at the IR emitter with a comparison value for the electric signal to achieve a comparison result forming a calibration information; wherein, when performing the in-situ calibration, the calibration information is applicable to the photoacoustic sensor for adjusting the IR emitter and/or is applicable to an output signal of the photoacoustic sensor for correcting the output signal.

2. Apparatus 2 according to example 1, wherein the calibration unit 10 is configured to adjust the current electric signal based on the comparison result to obtain a target value of the electric signal at the IR emitter to perform the in-situ calibration.

3. Apparatus 2 according to example 1 or 2, further comprising: a processing unit 15 configured to process the output signal of the photoacoustic sensor based on the calibration information to obtain an adjusted output signal of the photoacoustic sensor.

4. Apparatus 2 according to any of examples 1 to 3, wherein the calibration unit is configured to adjust the target value of the electric signal such that a target value of a physical characteristic of the IR emitter 6 is obtained.

5. Apparatus 2 according to any of examples 1 to 4, wherein the calibration unit 10 is configured to adjust the current electric signal 18 such that a change of resistance of the IR emitter is compensated.

6. Apparatus 2 according to any of examples 1 to 5, wherein the current electric signal 18 comprises an electric pulse and wherein the calibration unit 10 is configured to calculate a time constant of the photoacoustic sensor 4 from a current physical characteristic based on the electric pulse, wherein the time constant indicates an ability of the current physical characteristic to follow the electric pulse.

7. Apparatus according to any of examples 1 to 6, wherein the current electric signal 18 comprises an electric pulse and wherein the calibration unit 10 is configured to adjust the electric pulse such that at least one of an edge steepness, an amplitude, or a repetition frequency of the electric pulse is changed; wherein the change of the electric pulse changes the physical characteristic of the IR emitter such that the absolute difference between a current physical characteristic and the target value of the physical characteristic is reduced.

8. Apparatus 2 according to any of examples 1 to 7, wherein the current electric signal comprises an electric pulse and wherein a current physical characteristic is different from the target value of the physical characteristic due to a degradation of the IR emitter 6 and wherein the calibration unit 10 is configured to adjust a current electric signal or the electric pulse such that the degradation of the IR emitter is compensated.

9. Apparatus (2') for in-situ calibration of a photoacoustic sensor (4), the apparatus (2) comprising: a calibration unit (10) configured to control a signal generator (12) such that the signal generator feeds the IR emitter with an electric pulse; a sensing unit (8') configured to detect a current physical characteristic of a surface of the IR emitter (6), wherein the current physical characteristic of the IR emitter depends on the electric pulse; wherein the calibration unit is configured to compare the current physical characteristic of the surface of the IR emitter (6) with a target value of the physical characteristic of the surface of the IR emitter to obtain a calibration signal (11') forming a calibration information, wherein, when performing the in-situ calibration, the calibration information is applicable to the signal generator (12) for adjusting the IR emitter and/or is applicable to an output signal of the photoacoustic sensor for correcting the output signal.

10. Apparatus (2') according to example 9, wherein the calibration unit (10) is configured to adjust the electric pulse of the signal generator (12) based on the calibration information to perform the in-situ calibration.

11. Apparatus (2') according to example 9 or 10, further comprising: a processing unit (15) configured to process an output signal of the photoacoustic sensor based on the calibration information to obtain an adjusted output signal of the photoacoustic sensor.

12. Apparatus (2') according to any of examples 9 to 11, wherein the sensing unit is configured to measure a temperature of the surface of the IR emitter (6) using determining a temperature of an environment of the IR emitter; or wherein the sensing unit (8') is configured to measure an infrared radiation of the IR emitter (6) at the surface of the IR emitter.

13. Apparatus (2') according to any of examples 9 to 12, wherein the apparatus (2') comprises the signal generator (12), wherein the signal generator is configured to generate the electric pulse and to feed the IR emitter (6) of the photoacoustic sensor (4) with the electric pulse.

14. Apparatus (2') according to any of examples 9 to 13, wherein the calibration unit is configured to calculate a time constant of the photoacoustic sensor (4) from the current physical characteristic based on the electric pulse, wherein the time constant indicates an ability of a current physical characteristic to follow the electric pulse.

15. Apparatus (2') according to any of examples 9 to 14, wherein the calibration unit is configured to adjust the electric pulse such that at least one of an edge steepness, an amplitude, or a repetition frequency of the electric pulse is changed; wherein the change of the electric pulse changes the physical characteristic of the IR emitter (6) such that the absolute difference between the current physical characteristic and the target value of the physical characteristic is reduced.

16. Apparatus (2') according to any of examples 9 to 15, wherein the current physical characteristic is different from the target value of the physical characteristic due to a degradation of the IR emitter and wherein the calibration unit is configured to adjust the electric pulse such that the degradation of the IR emitter (6) is compensated.

17. Microelectromechanical system (100) comprising: an apparatus (2') according to any of examples 9 to 16, wherein the apparatus and the IR emitter of the photoacoustic sensor are formed in a common semiconductor substrate; wherein the sensing unit (8') comprises a semiconductor sensing unit formed within the semiconductor substrate.

18. Apparatus or microelectromechanical system according to any of examples 1 to 17, wherein the physical characteristic comprises a temperature or an emissivity or a radiation of an electromagnetic signal of the IR emitter.

19. Use of an apparatus according to any of examples 1 to 16 or the microelectromechanical system according to example 17 to perform a method described herein.

It is to be understood that in this specification, the signals on lines are sometimes named by the reference numerals for the lines or are sometimes indicated by the reference numerals themselves, which have been attributed to the lines. Therefore, the notation is such that a line having a certain signal is indicating the signal itself. A line can be a physical line in a hardwired implementation. In a computerized implementation, however, a physical line does not exist, but the signal represented by the line is transmitted from one calculation module to the other calculation module. Moreover, the lines may be understood to be unidirectional or bidirectional depending on the context of the embodiment. Hence, the (corresponding) signals may be understood to be unidirectional or bidirectional as well.

Although the present invention has been described in the context of block diagrams where the blocks represent actual or logical hardware components, the present invention can also be implemented by a computer-implemented method. In the latter case, the blocks represent corresponding method steps where these steps stand for the functionalities performed by corresponding logical or physical hardware blocks.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some embodiments, some one or more of the most important method steps may be executed by such an apparatus.

The inventive transmitted or encoded signal can be stored on a digital storage medium or can be transmitted on a transmission medium such as a wireless transmission medium or a wired transmission medium such as the Internet.

Depending on certain implementation requirements, embodiments of the invention can be implemented in hardware or in software. The implementation can be performed using a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the inventive method is, therefore, a computer program having a program code for performing one of the methods described herein, when the computer program runs on a computer.

A further embodiment of the inventive method is, therefore, a data carrier (or a non-transitory storage medium such as a digital storage medium, or a computer-readable medium) comprising, recorded thereon, the computer program for performing one of the methods described herein. The data carrier, the digital storage medium or the recorded medium are typically tangible and/or non-transitory.

A further embodiment of the invention method is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a microprocessor in order to perform one of the methods described herein. Generally, the methods are preferably performed by any hardware apparatus.

The above described embodiments are merely illustrative for the principles of the present invention. It is understood that modifications and variations of the arrangements and the details described herein will be apparent to others skilled in the art. It is the intent, therefore, to be limited only by the scope of the impending patent claims and not by the specific details presented by way of description and explanation of the embodiments herein.

What is claimed is:
1. A calibration system for in-situ calibration of a photoacoustic sensor, the calibration system comprising:

the photoacoustic sensor comprising:
- a light emitter configured to emit light along a transmission path to a gas; and
- an acoustic sensor element configured to detect an acoustic signal emitted from the gas based on received light and generate an output signal based on the detected acoustic signal; and a calibration apparatus comprising:
- a first radiation sensor configured to detect the light transmitted along the transmission path and to provide an information signal based on the detected light; and
- a calibration unit, comprising at least one processor, configured to receive the information signal from the first radiation sensor and to provide a calibration information based on the information signal from the first radiation sensor.

2. The calibration system according to claim 1, wherein the first radiation sensor is located at a first distance to the acoustic sensor element and at a second distance to the light emitter, wherein the first distance is smaller than the second distance.

3. The calibration system according to claim 2, further comprising:
- a second radiation sensor configured to detect a current physical characteristic of the light emitter at a position different from a position of the first radiation sensor, and
- wherein the second radiation sensor is located in a spatial position that is closer to the light emitter when compared to a spatial position of the first radiation sensor, or
- wherein the second radiation sensor is located at a third distance to the light emitter, wherein the third distance is smaller than the second distance.

4. The calibration system according to claim 3, wherein the calibration unit is configured to determine, based on a difference of a physical characteristic measured by the first radiation sensor and the current physical characteristic measured by the second radiation sensor, whether to apply the calibration information to a signal generator for adjusting the light emitter or to apply the calibration information to the output signal of the acoustic sensor element for correcting the output signal.

5. The calibration system according to claim 1, wherein the first radiation sensor is located at a spatial position such that the light detected from the first radiation sensor and the light reaching the gas are both attenuated by a same amount.

6. The calibration system according to claim 1, wherein the first radiation sensor is located at a spatial position with respect to the acoustic sensor element such that a length of an effective transmission path of a physical characteristic to the acoustic sensor element and to the first radiation sensor differs by not more than 20%.

7. The calibration system according to claim 1, wherein the calibration unit is configured to adjust at least one physical characteristic of the light emitter based on the calibration information to perform the in-situ calibration.

8. The calibration system according to claim 7, wherein the physical characteristic comprises a temperature of the light emitter, an emissivity of the light emitter, or a radiation of an electromagnetic signal of the light emitter.

9. The calibration system according to any of claim 1, further comprising:
- a processing unit configured to process the output signal of the acoustic sensor element based on the calibration information to obtain an adjusted output signal of the acoustic sensor element.

10. The calibration system according to claim 1, wherein the light emitter is configured to emit light pulses of different characteristics.

11. The calibration system according to claim 10, wherein the different characteristics include at least one characteristic selected from a group of characteristics including a different repetition frequency of the light pulses, a different shape of the light pulses, and a different light spectrum.

12. The calibration system according to claim 1, wherein the first radiation sensor provides the information signal based on a light pulse having a characteristic different from a characteristic of a light pulse used for photoacoustic measurement.

13. The calibration system according to claim 1, further comprising:
- a second radiation sensor configured to detect a current physical characteristic of the light emitter, wherein the calibration unit comprises a threshold switch configured to signal a signal generator to stop feeding the light emitter with an electric signal on a condition a physical characteristic corresponding to the current physical characteristic exceeds a threshold value.

14. The calibration system according to claim 13, wherein the threshold switch comprises a hysteresis such that when falling behind a further threshold value, the signal generator starts feeding the light emitter with the electric signal.

15. The calibration system according to claim 13, wherein the second radiation sensor is configured to measure a temperature of a surface of the light emitter by determining a temperature of an environment of the light emitter, or
- wherein the first radiation sensor is configured to determine a temperature of the light emitter based on the detected light transmitted along the transmission path.

16. The calibration system according to claim 1, further comprising:
- a signal generator configured to generate an electric signal and feed the light emitter with the electric signal.

17. The calibration system according to claim 16, wherein the calibration unit is configured to control the signal generator such that the signal generator feeds the light emitter with an electric pulse.

18. The calibration system according to claim 17, wherein the calibration unit is configured to adjust the electric pulse such that at least one of an edge steepness, an amplitude, or a repetition frequency of the electric pulse is changed.

19. The calibration system according to claim 1, wherein, when performing an in-situ calibration, the first radiation sensor provides the information signal based on light signals generated in a regular measurement on a measurement gas.

20. The calibration system according to claim 1, wherein: the light emitter, the acoustic sensor element, the first radiation sensor, and the calibration unit are formed in a common semiconductor substrate, and the first radiation sensor comprises a semiconductor sensor formed within the semiconductor substrate.

21. A method for in-situ calibration of a photoacoustic sensor, the method comprising:
- emitting light along a transmission path to a gas;
- detecting, by an acoustic sensor element of the photoacoustic sensor, an acoustic signal emitted from the gas based on received light;
- generate, by the acoustic sensor element, an output signal based on the detected acoustic signal;

detecting, by a radiation sensor, the light transmitted along the transmission path;
generating, by the radiation sensor, an information signal based on the detected light;
receiving, by a calibration unit, the information signal from the radiation sensor; and
providing, by the calibration unit, calibration information based on the information signal from the radiation sensor.

* * * * *